United States Patent
Kassambara et al.

(10) Patent No.: US 12,071,671 B2
(45) Date of Patent: Aug. 27, 2024

(54) METHODS FOR THE IN VITRO DETERMINATION OF THE OUTCOME AND FOR THE TREATMENT OF INDIVIDUALS HAVING MULTIPLE MYELOMA

(71) Applicants: CENTRE NATIONAL DE LA RECHERCHE SCIENTIFIQUE, Paris (FR); UNIVERSITE DE MONTPELLIER, Montpellier (FR); CENTRE HOSPITALIER UNIVERSITAIRE DE MONTPELLIER, Montpellier (FR)

(72) Inventors: Alboukadel Kassambara, Marvejols (FR); Jérôme Moreaux, Montpellier (FR); Wafa Hassen, Montpellier (FR)

(73) Assignees: CENTRE NATIONAL DE LA RECHERCHE SCIENTIFIQUE, Paris (FR); UNIVERSITE DE MONTPELLIER, Montpellier (FR); CENTRE HOSPITALIER UNIVERSITAIRE DE MONTPELLIER, Montpellier (FR)

(*) Notice: Subject to any disclaimer, the term of this patent is extended or adjusted under 35 U.S.C. 154(b) by 1002 days.

(21) Appl. No.: 16/968,448

(22) PCT Filed: Feb. 7, 2019

(86) PCT No.: PCT/EP2019/052992
§ 371 (c)(1),
(2) Date: Aug. 7, 2020

(87) PCT Pub. No.: WO2019/154905
PCT Pub. Date: Aug. 15, 2019

(65) Prior Publication Data
US 2020/0399709 A1    Dec. 24, 2020

(30) Foreign Application Priority Data
Feb. 8, 2018    (EP) .................................. 18305136

(51) Int. Cl.
*C12Q 1/6886* (2018.01)
*G16B 25/10* (2019.01)
*G16B 40/00* (2019.01)
*G16H 10/40* (2018.01)
*G16H 20/10* (2018.01)

(52) U.S. Cl.
CPC .......... *C12Q 1/6886* (2013.01); *G16B 25/10* (2019.02); *G16B 40/00* (2019.02); *G16H 10/40* (2018.01); *G16H 20/10* (2018.01); *C12Q 2600/106* (2013.01); *C12Q 2600/118* (2013.01); *C12Q 2600/158* (2013.01)

(58) Field of Classification Search
CPC .......... C12Q 1/6886; C12Q 2600/106; C12Q 2600/118; C12Q 2600/158; G16H 10/40
See application file for complete search history.

(56) References Cited

U.S. PATENT DOCUMENTS

2019/0218618 A1*    7/2019    Klijn .................... C12Q 1/686

FOREIGN PATENT DOCUMENTS

| EP | 1 964 930 | 9/2008 | |
|---|---|---|---|
| WO | WO-2008086182 A2 * | 7/2008 | ......... G01N 33/5011 |
| WO | 2010/078531 | 7/2010 | |
| WO | 2015/144929 | 10/2015 | |

OTHER PUBLICATIONS

Lipchick, B.C., Fink, E.E. and Nikiforov, M.A.. Oxidative stress and proteasome inhibitors in multiple myeloma. Pharmacological research, 105, pp. 210-215. (Year: 2016).*

Bustany, S., Bourgeais, J., Tchakarska, G., Body, S., Hérault, O., Gouilleux, F. and Sola, B. Cyclin D1 unbalances the redox status controlling cell adhesion, migration, and drug resistance in myeloma cells. Oncotarget, 7(29), p. 45214-45224. (Year: 2016).*

Bustany, S., Bourgeais, J., Tchakarska, G., Body, S., Hérault, O., Gouilleux, F. and Sola, B. Cyclin D1 unbalances the redox status controlling cell adhesion, migration, and drug resistance in myeloma cells. Oncotarget, 7(29), Supplementary Methods, p. 1-5. (Year: 2016).*

International Search Report for PCT/EP2019/052992 dated May 20, 2019, 7 pages.

Written Opinion of the ISA for PCT/EP2019/052992 dated May 20, 2019, 11 pages.

Barlogie, B. et al., "Total therapy 2 without thalidomide in comparison with total therapy 1: role of intensified induction and posttransplantation consolidation therapies," Blood, Apr. 1, 2006, vol. 107, No. 7, p. 2633-2638.

(Continued)

*Primary Examiner* — Kaitlyn L Minchella
*Assistant Examiner* — Janna Nicole Schultzhaus
(74) *Attorney, Agent, or Firm* — NIXON & VANDERHYE

(57) ABSTRACT

Disclosed is a method for in vitro predicting the outcome of an individual having a multiple myeloma, including: —a) measuring the expression level of at least 2 genes encoding a ROS detoxifying (AOX) protein selected in a group including AKR1 B1, ARNT, CAT, CBR1, DHCR24, EGLN1, GLRX2, HIF1A, MGST1, MSRB1, PRDX6, SLC7A11, SOD1, SRXN1, TALDO1 and TXN and/or the expression level of at least 2 genes encoding ROS producing (ROS) protein selected in a group including CYBA, CYB5A, CYC1, NCF1B, NCF1C, NCF4, NDUFA12, NDUFS2, NDUFS8, SHC1 and UQCR10, in a biological sample obtained from the individual; —b) calculating an AOX score value and/or a ROS score value from the respective expression level(s) obtained at step a); —c) classifying the individual as having a good prognosis status or a bad prognosis status, by comparing the score value obtained at step b) with a reference score value.

8 Claims, 15 Drawing Sheets

(56) References Cited

OTHER PUBLICATIONS

Decaux, O. et al., "Prediction of Survival in Multiple Myeloma Based on Gene Expression Profiles Reveals Cell Cycle and Chromosomal Instability Signatures in High-Risk Patients and Hyperdiploid Signatures in Low-Risk Patients: A Study of the Intergroupe Francophone du Myélome," J Clin Oncol 26, Aug. 20, 2008, p. 1-21.
DeNicola. G. M. et al., "Oncogene-induced Nrf2 transcription promotes ROS detoxification and tumorigenesis," Nature, vol. 475, Jul. 7, 2011, p. 106-109.
Diehn, M. et al., "Association of reactive oxygen species levels and radioresistance in cancer stem cells," Nature, vol. 458, Apr. 2009, p. 780-783.
Goldschmidt, H. et al., "Joint HOVON-50/GMMG-HD3 randomized trial on the effect of thalidomide as part of a high-dose therapy regimen and as maintenance treatment for newly diagnosed myeloma patients," Ann Hematol (2003) 82:654-659.
Hose, D. et al., "Proliferation is a central independent prognostic factor and target for personalized and risk-adapted treatment in multiple myeloma," haematologica 2011; 96(1), p. 87-95.
Irwin, M. et al., "Redox Control of Leukemia: From Molecular Mechanisms to Therapeutic Opportunities," Antioxidants & Redox Signaling, vol. 18, No. 11, 2013, p. 1349-1383.
Kassambara, A. et al., "GenomicScape: An Easy-to-Use Web Tool for Gene Expression Data Analysis. Application to Investigate the Molecular Events in the Differentiation of B Cells into Plasma Cells," PLoS Comput Biol 11(1): e1004077, Jan. 29, 2015, p. 1-10.
Kobayashi, C. and Suda, T., "Regulation of Reactive Oxygen Species in Stem Cells and Cancer Stem Cells," J. Cell. Physiol. 227: 421-430, 2012.
Mulligan, G. et al., "Gene expression profiling and correlation with outcome in clinical trials of the proteasome inhibitor bortezomib," Blood, Apr. 15, 2007, vol. 109, No. 8, p. 3177-3188.
Moreaux, J. et al., "Gene expression-based prediction of myeloma cell sensitivity to histone deacetylase inhibitors," British Journal of Cancer (2013), 1-10.
Moreaux, J. et al., "Development of Gene Expression-Based Score to Predict Sensitivity of Multiple Myeloma Cells to DNA Methylation Inhibitors," Mol Cancer Ther; 11(12) Dec. 2012, p. 1-8.
Moreaux, J. et al., "A high-risk signature for patients with multiple myeloma established from the molecular classification of human myeloma cell lines," haematologica 2011; 96(4), p. 574-582.
Réme, T. et al., "Modeling risk stratification in human cancer," Bioinformatics Advance Access published Apr. 2, 2013, p. 1-9.
Ren, F. et al., "New insights into redox regulation of stem cell self-renewal and differentiation," Biochimica et Biophysica Acta 1850 (2015) 1518-1526.
Sharma, A. et al., "Study of antioxidant levels in patients with multiple myeloma," Leukemia & Lymphoma, 50:5, 809-815.
Shaughnessy, J. et al., "A validated gene expression model of high-risk multiple myeloma is defined by deregulated expression of genes mapping to chromosome 1," Blood, Mar. 15, 2007, vol. 109, No. 6, p. 2276-2284.
Sporn, M. and Liby, K., "NRF2 and cancer: the good, the bad and the importance of context," Nature Reviews Cancer, vol. 12, Aug. 2012, p. 564-571.
Tarte, K. et al., "Induced Expression of B7-1 on Myeloma Cells Following Retroviral Gene Transfer Results in Tumor-Specific Recognition by Cytotoxic T Cells," J Immunol 1999; 163:514-524.
Urao, N. and Ushio-Fukai, M., "Redox Regulation of Stem/ Progenitor Cells and Bone Marrow Niche," Free Radic Biol Med. Jan. 2013 ; 54: 26-39.
Wang, K. et al., "Redox homeostasis: the linchpin in stem cell self-renewal and differentiation," Cell Death and Disease (2013) 4, e537, p. 1-10.
Ye, Z-H. et al., "Oxidative stress, redox regulation and diseases of cellular differentiation," Biochimica et Biophysica Acta 1850 (2015) 1607-1621.

\* cited by examiner

METHODS FOR THE IN VITRO DETERMINATION OF THE OUTCOME AND FOR THE TREATMENT OF INDIVIDUALS HAVING MULTIPLE MYELOMA

This application is the U.S. national phase of International Application No. PCT/EP2019/052992 filed Feb. 7, 2019 which designated the U.S. and claims priority to European Patent Application No. 18305136.6 filed Feb. 8, 2018, the entire contents of each of which are hereby incorporated by reference.

TECHNICAL FIELD

The present invention relates to the prognosis of individuals having multiple myeloma (MM) and the prediction of the likelihood of said individuals to respond positively to a targeted therapeutic treatment. In particular, two scores may be calculated from the expression levels of respectively 16 genes encoding reactive oxygen species (ROS) detoxifying (AOX) proteins and 11 genes encoding ROS producing (ROS) proteins. Said scores are also indicative of the aggressiveness of the multiple myeloma disease.

BACKGROUND ART

Reactive oxygen species (ROS) are oxygen containing, highly reactive, chemical species constantly produced by enzymatic and non-enzymatic reactions in different cellular compartments. Excessive ROS production induces irreversible oxidation of macromolecules and leads to oxidative stress, which underlies several human diseases. Thus, redox homeostasis is fundamental for normal cellular functioning and is maintained by the net physiologic balance between production and removal of ROS through the tight regulation of both ROS-producing (inducer) and ROS-detoxifying (scavenger) pathways.

Multiple myeloma (MM) is the second most common hematologic malignancy and is the malignant counterpart of post-germinal centre cells. Several reports have underlined a major role of redox system in B malignancies. However, most of the research is restricted to chronic B cell malignancies and focuses on the redox status in response to therapy rather than on the baseline differences between normal and malignant B cells. Few are the available data about the relevance of the redox status for MM pathogenesis, the effectiveness or failure of chemotherapy, and prognosis value (Sharma et al., 2009).

Current knowledge highlights a critical role of redox regulation in differentiation, de-differentiation and tumorigenesis in different cellular settings. Cell differentiation is an astonishing process controlled and driven by specific signalling cascades rewiring where intracellular redox status appears to be a necessary and sufficient modulator to maintain the balance between self-renewal and differentiation in dividing cells (Ren et al., 2015; Urao et al., 2013; Wang et al., 2013; Ye et al., 2015; Kobayashi et al., 2011). Moreover, compared with their normal counterparts, tumor cells often sustain disturbed redox status, which is thought to accommodate the tumor proliferation and aggressiveness (Sporn et al., 2012; Diehn et al., 2009; Irwin et al., 2013; DeNicola et al., 2012).

Although it was considered incurable for a long time, recent developments in cancer research have provided treatment strategies leading to an overall survival of intensively-treated patients of 6-7 years and an event-free survival of 3-4 years. However, patients invariably relapse after multiple lines of treatment, with shortened intervals in between relapses, and finally become resistant to any treatment, resulting in loss of clinical control over the disease and death within weeks.

Despite these recent advances in cancer research, the proposed therapeutic approaches often depend on the patient's age only, and thus are not adapted to an individual patient or even a subgroup of patients.

Taken into account the current growing tendency for therapy providers in developing personalized diagnostic and therapeutic approaches, there is therefore an urgent need to provide individuals having MM with an accurate diagnosis of the disease intended to lead to the most adapted treatment.

SUMMARY OF INVENTION

One aspect of the invention relates to a method for in vitro predicting the outcome of an individual having a multiple myeloma, comprising the steps of:

a) measuring the expression level of at least 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN and/or the expression level of at least 2 genes encoding ROS producing (ROS) protein selected in a group comprising CYBA, CYB5A, CYC1, NCF1B, NCF1C, NCF4, NDUFA12, NDUFS2, NDUFS8, SHC1 and UQCR10, in a biological sample obtained from said individual;

b) calculating an AOX score value and/or a ROS score value from the said respective expression level(s) obtained at step a);

c) classifying the said individual as having a good prognosis status or a bad prognosis status, by comparing the score value obtained at step b) with a reference score value.

Another aspect of the invention relates to a method for in vitro predicting the likelihood of an individual having a multiple myeloma to respond to a therapeutic anti-MM treatment, comprising the steps of:

a) measuring the expression level of at least 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and the expression level of at least 2 genes encoding ROS producing (ROS) protein selected in a group comprising CYBA, CYB5A, CYC1, NCF1B, NCF1C, NCF4, NDUFA12, NDUFS2, NDUFS8, SHC1 and UQCR10, in a biological sample obtained from an individual having a multiple myeloma;

b) calculating a AOX score value and a ROS score value from the said respective expression levels obtained at step a);

c) classifying the said individual as being a responsive individual or a non-responsive individual, by comparing each score value obtained at step b) with a reference score value.

In a still other aspect, the invention relates to the use of the expression level of at least 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and/or the expression level of at least 2 genes encoding ROS producing (ROS) protein selected in a group comprising CYBA, CYB5A, CYC1, NCF1B, NCF1C, NCF4, NDUFA12, NDUFS2, NDUFS8, SHC1 and UQCR10, to calculate an AOX score value and/or a ROS score value representing a biomarker for assessing the aggressiveness of a multiple myeloma disease in an individual having a multiple myeloma.

Another aspect of the invention relates to the use of the expression level of at least 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and/or the expression level of at least 2 genes encoding ROS producing (ROS) protein selected in a group comprising CYBA, CYB5A, CYC1, NCF1B, NCF1C, NCF4, NDUFA12, NDUFS2, NDUFS8, SHC1 and UQCR10, to calculate an AOX score value and/or a ROS score value representing a biomarker for predicting the outcome of an individual having a multiple myeloma.

An additional aspect of the invention relates to the use of the expression level of at least 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and the expression level of at least 2 genes encoding ROS producing (ROS) protein selected in a group comprising CYBA, CYB5A, CYC1, NCF1B, NCF1C, NCF4, NDUFA12, NDUFS2, NDUFS8, SHC1 and UQCR10, to calculate an AOX score value and a ROS score value representing a biomarker for predicting the likelihood of an individual having a multiple myeloma to respond to a therapeutic anti-MM treatment.

Finally, the invention also relates to an anticancer compound or a combination thereof for use in treating multiple myeloma in an individual in need thereof, wherein said individual is classified as being a responsive individual by the method disclosed herein.

DETAILED DESCRIPTION OF THE INVENTION

Figure 1:
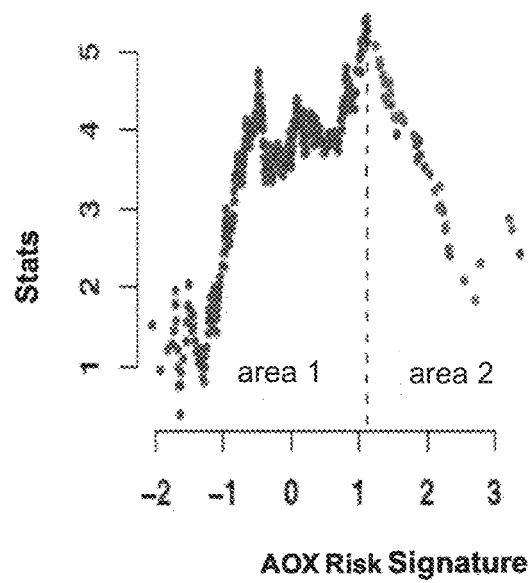
FIG. 1 is a diagram representing patients of the TT2 cohort ranked according to increasing AOX risk signature. Maxstat function was used to identify the 1.11 cut off points (dashed line) and to further distinguish patients with a low (area 1) from patients with a high (area 2) AOX risk signature.

The inventors have identified two set of genes, namely 16 genes encoding a ROS detoxifying (AOX) protein and 11 genes encoding a ROS producing (ROS) protein, which genes are differentially expressed in individuals having a multiple myeloma as compared to healthy individuals. A score value for each set of genes may be calculated, taking into account the beta coefficient for each gene based on the Cox statistical model. The AOX score value is calculated from the differential expression of the 16 genes encoding a ROS detoxifying protein, whereas the ROS score value is calculated from the differential expression of the 11 genes encoding a ROS producing protein. The determination of a cut off value for each of the two score values allows discriminating individuals having a low AOX score value from individuals having a high AOX score value, and individuals having a low ROS score value from individuals having a high ROS score value.

Since both a AOX score value and a ROS score value may be calculated, 3 subpopulations of individuals may be further discriminated:
  individuals having a low AOX score value and a low ROS (low AOX/ROS) score value;
  individuals (i) having a low AOX score value and a high ROS score value or individuals (ii) having a high AOX score value and a low ROS score value; and
  individuals having a high AOX score value and a high ROS (high AOX/ROS) score value.

Said score values may be advantageously implemented for prognosis purposes, i.e. to assist physicians in classifying individuals affected with multiple myeloma (MM) as (i) poor prognosis status individuals or (ii) good prognosis status individuals.

In particular, the inventors have shown that the score values described herein and obtained from individuals having a multiple myeloma may be significantly correlated with the ability of said individuals to respond to a targeted therapeutic treatment.

The inventors have shown that individuals with poor prognosis status, in particular individuals having a high AOX/ROS score, were found to be endowed with a poor sensitivity to a cytostatic alkylating agent, notably to a bifunctional cytostatic alkylating agent, such as melphalan and/or to a proteasome inhibitor, such as bortezomib, as compared to the individuals having a good prognosis status, namely the individuals having a low AOX/ROS score, which latter individuals display better sensitivity to any one of these drugs.

Without wishing to be bound by any particular theory, the inventors believe that the prognosis AOX and/or ROS scores described herein, which are based on the expression profile of the two sets of 16 and 11 genes and/or proteins specified herein, reflect the degree of severity of the multiple myeloma disease, and therefore provide a tool for implementing the personalized medicine concept for diagnosis and treatment of individuals affected with MM.

Within the scope of the present invention, the terms "score", "score value", "score signature" and "risk signature" are considered as being equivalent terms.

Within the scope of the present invention, the term "individual" refers to a human individual or to a non-human animal, preferably to a mammal, and most preferably to a human individual.

The expression "multiple myeloma individual" refers to an individual having a multiple myeloma.

The expression "multiple myeloma" (also referred as 'MM') refers to the multiple myeloma disease such as defined by class C90.0 in accordance with the International Classification of Diseases World Health Organisation Classification (10th revised edition; 2016).

The term "outcome" refers to the survival, the relapse or the death of the individual. The outcome may relate to disease-free survival (DFS), event free survival (EFS) or overall survival (OS), as defined within the state of the art. Illustratively, a "bad outcome" may refer to a disease relapse or death of the individual. Oppositely, a "good outcome" may refer to survival of the individual, with or without relapse episode.

The expression "ROS detoxifying (AOX) protein" refers to a protein involved in the process of scavenging ROS.

The expression "ROS producing (ROS) protein" refers to a protein involved in the direct or indirect production of ROS.

The AKR1B1 gene (Entrez Gene 231) encodes the AKR1B1 protein (UniProtKB P15121), a member of the aldo/keto reductase superfamily. AKR1B1 is also known as Aldo-Keto Reductase Family 1 Member B, Aldo-Keto Reductase Family 1 Member B1, Aldose Reductase, EC 1.1.1.21, ALDR1, AR, Lii5-2 CTCL Tumor Antigen, Low Km Aldose Reductase, Aldehyde Reductase 1, Aldehyde Reductase, EC 1.1.1, ALR2 or ADR.

The ARNT gene (Entrez Gene 405) encodes the ARNT protein (UniProtKB P27540) that contains a basic helix-loop-helix domain and two characteristic PAS domains along with a PAC domain. ARNT is also known as Aryl Hydrocarbon Receptor Nuclear Translocator, Class E Basic Helix-Loop-Helix Protein 2, Dioxin Receptor, Nuclear Translocator, HIF-1-Beta, BHLHe2, Hypoxia-Inducible Factor 1, Beta Subunit, HIF1B and TANGO.

The CAT gene (Entrez Gene 847) encodes the CAT protein (UniProtKB P04040), a catalase. CAT is also known as Catalase and EC 1.11.1.6.

The CBR1 gene (Entrez Gene 873) encodes the CBR1 protein (UniProtKB P16152) that belongs to the short-chain dehydrogenases/reductases (SDR) family. CBR1 is also known as Carbonyl Reductase 1, Short Chain Dehydrogenase/Reductase Family 21C Member 1, NADPH-Dependent Carbonyl Reductase 1, Prostaglandin-E(2) 9-Reductase, Prostaglandin 9-Ketoreductase, EC 1.1.1.184, SDR21C1, CBR, 15-Hydroxyprostaglandin Dehydrogenase [NADP (+)], Carbonyl Reductase (NADPH) 1, EC 1.1.1.197, EC 1.1.1.189, HCBR1 and CRN.

The DHCR24 gene (Entrez Gene 1718) encodes the DHCR24 protein (UniProtKB Q15392), a Flavin adenine dinucleotide (FAD)-dependent oxidoreductase. DHCR24 is also known as 24-Dehydrocholesterol Reductase, Desmosterol-To-Cholesterol Enzyme, Diminuto/Dwarf1 Homolog, Seladin-1, 3 Beta-Hydroxysterol Delta 24-Reductase, Delta (24)-Sterol Reductase, Selective AD Indicator 1, EC 1.3.1.72, Nbla03646, KIAA0018 and DCE.

The EGLN1 gene (Entrez Gene 54583) encodes the EGLN1 protein (UniProtKB Q9GZT9) that catalyses the post-transcriptional formation of 4-hydroxyproline in hypnoxia-inducible factor (HIF) alpha proteins. EGLN1 is also known as Egl-9 Family Hypoxia Inducible Factor 1, Prolyl Hydroxylase Domain-Containing Protein 2, Hypoxia-Inducible Factor Prolyl Hydroxylase 2, HIF-Prolyl Hydroxylase 2, C1orf12, HIF-PH2, HPH-2, PHD2, Zinc Finger MYND Domain-Containing Protein 6, Egl Nine-Like Protein 1, Egl Nine Homolog 1, EC 1.14.11.29, EC 1.14.11, ZMYND6, ECYT3, HALAH, and SM-20.

The GLRX2 gene (Entrez Gene 51022) encodes the GLRX2 protein (UniProt KB Q9NS18), a member of the glutaredoxin family of proteins. GLRX2 is also known as Glutaredoxin 2, Glutaredoxin (Thioltransferase) 2, GRX2, BA101E13.1 (GRX2 Glutaredoxin (Thioltransferase) 2) and CGI-133.

The HIF1A gene (Entrez Gene 3091) encodes the HIF1A protein (UniProtKB Q16665), the alpha subunit of transcription factor hypoxia-inducible factor-1 (HIF-1). HIF1A is also known as Hypoxia Inducible Factor 1 Alpha Subunit, Class E Basic Helix-Loop-Helix Protein 78, Basic-Helix-Loop-Helix-PAS Protein MOP1, PAS Domain-Containing Protein 8, Member Of PAS Protein 1, HIF-1-Alpha, BHLHe78, PASD8, MOP1, Hypoxia-Inducible Factor 1 Alpha Isoform I.3, Hypoxia-Inducible Factor 1-Alpha, Member Of PAS Superfamily 1, HIF-1A, HIF1 and ARNT Interacting Protein.

The MGST1 gene (Entrez Gene 4257) encodes the MGST1 protein (UniProtKB P10620) that catalyzes the conjugation of glutathione to electrophiles and the reduction of lipids hydroperoxides. MGST1 is also known as Microsomal Glutathione S-Transferase 1, Microsomal GST-1, EC 2.5.1.18, GST12, MGST and Glutathione S-Transferase 12.

The MSRB1 gene (Entrez Gene 51734) encodes the MSRB1 protein (UniProtKB Q9NZV6) that belongs to the methionine-R-sulfoxide reductase B (MSRB) family. MSRB1 is also known as Methionine Sulfoxide Reductase B1, Selenoprotein X, 1, Selenoprotein R, Methionine-R-Sulfoxide Reductase B1, SEPX1, SELX, Selenoprotein X, EC 1.8.4.-, HSPC270, SELR and SepR.

The PRDX6 gene (Entrez Gene 9588) encodes the PRDX6 protein (UniProtKB P30041), a member of the thiol specific antioxidant protein family. PRDX6 is also known as Peroxiredoxin 6, Acidic Calcium-Independent Phospholipase A2, Non-Selenium Glutathione Peroxidase, Red Blood Cells Page Spot 12, Antioxidant Protein 2, Liver 2D Page Spot 40, 1-Cys Peroxiredoxin, 24 KDa Protein, EC 1.11.1.15, 1-Cys PRX, AiPLA2, NSGPx, AOP2, Epididymis Secretory Sperm Binding Protein Li 128m, EC 1.11.1.9, HEL-S-128m, EC 3.1.1.-, KIAA0106, 1-Cys, PRX and P29.

The SLC7A11 gene (Entrez Gene 23657) encodes the SLC7A11 protein (UniProtKB Q9UPY5), a member of a heterotrimeric, sodium-independent, anionic amino acid transport system. SLC7A11 is also known as Solute Carrier Family 7 Member 11, Calcium Channel Blocker Resistance Protein CCBR1, Amino Acid Transport System Xc-, XCT, CCBR1 and Cystine/Glutamate Transporter.

The SOD1 gene (Entrez Gene 6647) encodes the SOD1 protein (UniProtKB P00441) that is one of two isozymes responsible for destroying free superoxide radicals in the body. SOD1 is also known as Superoxide Dismutase 1, EC 1.15.1.1, HSod1, Amyotrophic Lateral Sclerosis 1, Epididymis Secretory Protein Li 44, Cu/Zn Superoxide Dismutase, Indophenoloxidase A, SOD, Soluble, Homodimer, HEL-S-44, ALS1, ALS, SOD and IPOA.

The SRXN1 gene (Entrez Gene 140809) encodes the SRXN1 protein (UniProtKB Q9BYN0) that contributes to oxidative stress resistance. SRXN1 is also known as Sulfiredoxin 1, C20orf139, SRX, EC 1.8.98.2, Npn3, Sulfiredoxin 1 Homolog (S. cerevisiae), Chromosome 20 Open Reading Frame 139 and SRX1.

The TALDO1 gene (Entrez Gene 6888) encodes the TALDO1 protein (UniProtKB P37837), a key enzyme of the nonoxidative pentose phosphate pathway. TALDO1 is also known as Transaldolase 1, EC 2.2.1.2, TALDOR, TAL, Testicular Secretory Protein Li 56, Dihydroxyacetone Transferase, Glycerone Transferase, Transaldolase, TAL-H, TALDO and TALH.

The TXN gene (Entrez Gene 7295) encodes the TXN protein (UniProtKB P10599) is part of the response to intracellular nitric oxide. TXN is also known as Thioredoxin, Surface-Associated Sulphydryl Protein, ATL-Derived Factor, SASP, TRX1, TRDX, ADF, TRX, Testicular Tissue Protein Li 199, Thioredoxin Delta 3 and TXN Delta 3.

The CYBA gene (Entrez Gene 1535) encodes the CYBA protein (UniProtKB P13498) the light, alpha subunit of cytochrome b. CYBA is also known as Cytochrome B-245 Alpha Chain, Superoxide-Generating NADPH Oxidase Light Chain Subunit, Neutrophil Cytochrome B 22 KDa Polypeptide, Flavocytochrome B-558 Alpha Polypeptide, Cytochrome B-245, Alpha Polypeptide, Cytochrome B(558) Alpha Chain, Cytochrome B558 Subunit Alpha, P22 Phagocyte B-Cytochrome, P22-PHOX, P22phox, Cytochrome B(558) Alpha-Subunit, Cytochrome B, Alpha Polypeptide, Cytochrome B-245 Light Chain and Cytochrome B Light Chain.

The CYB5A gene (Entrez Gene 1528) encodes the CYB5A protein (UniProtKB P00167), a membrane-bound cytochrome. CYB5A is also known as Cytochrome B5 Type A, CYB5, MCB5, Microsomal Cytochrome B5 Type A, Cytochrome B5 (Microsomal) the, Cytochrome B-5 and Type 1 Cyt-B5.

The CYC1 gene (Entrez Gene 1537) encodes the CYC1 protein (UniProtKB P08574), a subunit of the cytochrome bc1 complex. CYC1 is also known as Cytochrome C1, Ubiquinol-Cytochrome-C Reductase Complex Cytochrome C1 Subunit, Cytochrome B-C1 Complex Subunit 4, Complex III Subunit IV, Complex III Subunit 4, Cytochrome C-1, Cytochrome C1, Heme Protein, Mitochondrial, MC3DN6 and UQCR4.

The NCF1B gene (Entrez Gene 654816) encodes the NCF1B protein (UniProtKB A6NI72). NCF1B is also known as Neutrophil Cytosolic Factor 1B Pseudogene, Putative SH3 And PX Domain-Containing Protein 1B, SH3PXD1B, NCF-1B, Putative Neutrophil Cytosol Factor 1B and Neutrophil Cytosolic Factor 1B.

The NCF1C gene (Entrez Gene 65817) encodes the NCF1C protein (UniProtKB A8MVU1), the 75 kDa cytosolic subunit of neutrophil NADPH oxidase. NCF1C is also known as Neutrophil Cytosolic Factor 1C Pseudogene, SH3PXD1C, Putative SH3 And PX Domain-Containing Protein 1C, Neutrophil Cytosolic Factor 1C and NCF-1C.

The NCF4 gene (Entrez Gene 4689) encodes the NCF4 protein (UniProtKB Q15080), a cytosolic component of the superoxide-producing phagocyte NADPH-oxidase. NCF4 is also known as Neutrophil Cytosolic Factor 4, Neutrophil NADPH Oxidase Factor 4, SH3 And PX Domain-Containing Protein 4, Neutrophil Cytosolic Factor 4, 40 kDa, P40-Phox, SH3PXD4, Neutrophil Cytosol Factor 4, CGD3 and NCF.

The NDUFA12 gene (Entrez Gene 55967) encodes the NDUFA12 protein (UniProtKB Q9UI09), a part of the oxidative phosphorylation system in mitochondria. NDUFA12 is also known as NADH: Ubiquinone Oxidoreductase Subunit A12, NADH Dehydrogenase (Ubiquinone) 1 Alpha Subcomplex, 12, NADH-Ubiquinone Oxidoreductase Subunit B17.2, 13 KDa Differentiation-Associated Protein, Complex I B17.2 Subunit, CI-B17.234, DAP13, NADH Dehydrogenase [Ubiquinone] 1 Alpha Subcomplex Subunit 12, Complex I-B17.2, CIB 17.2 and B17.2.

The NDUFS2 gene (Entrez Gene 4720) encodes the NDUFS2 protein (UniProtKB O75306), a core subunit of the mitochondrial membrane respiratory chain NADH dehydrogenase (complex I). NDUFS2 is also known as NADH: Ubiquinone Oxidoreductase Core Subunit S2, NADH Dehydrogenase (Ubiquinone) Fe—S Protein 2, 49 kDa (NADH-Coenzyme Q Reductase), NADH Dehydrogenase [Ubiquinone] Iron-Sulfur Protein 2, Mitochondrial, NADH-Ubiquinone Oxidoreductase 49 KDa Subunit, Complex I 49 kDa Subunit, Complex I-49KD, CI-49 kD, NADH Dehydrogenase (Ubiquinone) Fe—S Protein 2 (49 kD) (NADH-Coenzyme Q Reductase), Complex 1, Mitochondrial Respiratory Chain, 49-KD Subunit, NADH-Ubiquinone Oxidoreductase NDUFS2 Subunit, EC 1.6.99.5, EC 1.6.99.3, EC 1.6.5.3 and CI-49.

The NDUFS8 gene (Entrez Gene 4728) encodes the NDUFS8 protein (UniProtKB O00217), a subunit of mitochondrial NADH:ubiquinone oxidoreductase. NDUFS8 is also known as NADH: Ubiquinone Oxidoreductase Core Subunit S8, NADH Dehydrogenase (Ubiquinone) Fe—S Protein 8, 23 kDa (NADH-Coenzyme Q Reductase), NADH Dehydrogenase [Ubiquinone] Iron-Sulfur Protein 8, Mitochondrial, NADH-Ubiquinone Oxidoreductase 23 KDa Subunit, Complex I 23 kDa Subunit, Complex I-23 kD, NADH Dehydrogenase (Ubiquinone) Fe—S Protein 8 (23 kD) (NADH-Coenzyme Q Reductase), TYKY Subunit, EC 1.6.99.5, EC 1.6.99.3, EC 1.6.5.3, CI-23 kD, CI-23k, CI23KD and TYKY.

The SHC1 gene (Entrez Gene 6464) encodes the SHC1 protein (UniProtKB P29353) three main isoforms that are adapter proteins in signal transduction pathways. SHC1 is also known as SHC Adaptor Protein 1, SHC-Transforming Protein 3, SHC-Transforming Protein A, SH2 Domain Protein C1, SHCA, SHC, Src Homology 2 Domain-Containing-Transforming Protein C1 and SHC-Transforming Protein 1.

The UQCR10 gene (Entrez Gene 29796) encodes the UQCR10 protein (UniProtKB Q9UDW1), a subunit of mitochondrial complex III. UQCR10 is also known as Ubiquinol-Cytochrome C Reductase, Complex III Subunit X, Ubiquinol-Cytochrome C Reductase, Complex III Subunit X, 7.2 kDa, Ubiquinol-Cytochrome C Reductase Complex 7.2 KDa Protein, Cytochrome C1 Non-Heme 7 KDa Protein, Complex III Subunit 9, UCRC, Ubiquinol-Cytochrome C Reductase Complex (7.2 KD), Cytochrome C1, Nonheme 7 kDa Protein, Cytochrome B-C1 Complex Subunit 9, Complex III Subunit X, HSPC051, HSPC119, HSPC151, UCCR7.2 and QCR9.

1/Survival Prognosis

One aspect of the invention relates to a method for in vitro predicting the outcome of an individual having a multiple myeloma, comprising the steps of:
- a) measuring the expression level of at least 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN and/or the expression level of at least 2 genes encoding ROS producing (ROS) protein selected in a group comprising CYBA, CYB5A, CYC1, NCF1B, NCF1C, NCF4, NDUFA12, NDUFS2, NDUFS8, SHC1 and UQCR10, in a biological sample obtained from said individual;
- b) calculating an AOX score value and/or a ROS score value from the said respective expression level(s) obtained at step a);
- c) classifying the said individual as having a good prognosis status or a bad prognosis status, by comparing the score value obtained at step b) with a reference score value.

Within the scope of the present invention, it has to be understood that:
the expression level of any combination of 2, 3, 4, 5, 6, 7, 8, 9, 10, 11, 12, 13, 14, 15 and 16 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN; and/or
the expression level of any combination of 2, 3, 4, 5, 6, 7, 8, 9, 10 and 11 genes encoding a ROS producing (ROS) protein selected in a group comprising CYBA, CYB5A, CYC1, NCF1B, NCF1C, NCF4, NDUFA12, NDUFS2, NDUFS8, SHC1 and UQCR10;
is of special interest.

In other words, each of the combination of 2, 3, 4, 5, 6, 7, 8, 9, 10, 11, 12, 13, 14, 15 and 16 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN; and/or each of the combination of 2, 3, 4, 5, 6, 7, 8, 9, 10 and 11 genes encoding a ROS producing (ROS) protein selected in a group comprising CYBA, CYB5A, CYC1, NCF1B, NCF1C, NCF4, NDUFA12, NDUFS2, NDUFS8, SHC1 and UQCR10 is explicitly disclosed herein.

In certain embodiments, the expression level of at least 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN and/or the expression level of at least 2 genes encoding a ROS producing (ROS) protein selected in a group comprising CYBA, CYB5A, CYC1, NCF1B, NCF1C, NCF4, NDUFA12, NDUFS2, NDUFS8, SHC1 and UQCR10 is measured in step a).

In certain embodiments, the expression level of at least 7 genes encoding a ROS detoxifying (AOX) protein and/or the expression level of at least 5 genes encoding ROS producing (ROS) protein is measured at step a).

Illustratively, the combination of 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is chosen in a group comprising each of the 120 possible combinations.

In some embodiments, the combination of 3 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is chosen in a group comprising each of the 560 possible combinations.

In some embodiments, the combination of 4 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is chosen in a group comprising each of the 1820 possible combinations.

In some embodiments, the combination of 5 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is chosen in a group comprising each of the 4368 possible combinations.

In some embodiments, the combination of 6 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is chosen in a group comprising each of the 8008 possible combinations.

In some embodiments, the combination of 7 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is chosen in a group comprising each of the 11440 possible combinations.

In some embodiments, the combination of 8 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is chosen in a group comprising each of the 12870 possible combinations.

In some embodiments, the combination of 9 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is chosen in a group comprising each of the 11440 possible combinations.

In some embodiments, the combination of 10 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is chosen in a group comprising each of the 8008 possible combinations.

In some embodiments, the combination of 11 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is chosen in a group comprising each of the 4368 possible combinations.

In some embodiments, the combination of 12 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is chosen in a group comprising each of the 1820 possible combinations.

In some embodiments, the combination of 13 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is chosen in a group comprising each of the 560 possible combinations.

In some embodiments, the combination of 14 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is chosen in a group comprising each of the 120 possible combinations.

In some embodiments, the combination of 15 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is chosen in a group comprising each of the 16 possible combinations.

In certain preferred embodiments, the expression level of each of the 16 genes encoding a ROS detoxifying (AOX) protein consisting of AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN is measured at step a).

In certain embodiments, the combination of 2 genes encoding a ROS producing (ROS) protein selected in a group comprising CYBA, CYB5A, CYC1, NCF1B, NCF1C, NCF4, NDUFA12, NDUFS2, NDUFS8, SHC1 and UQCR10 is chosen in a group comprising each of the 55 possible combinations.

In certain embodiments, the combination of 3 genes encoding a ROS producing (ROS) protein selected in a group comprising CYBA, CYB5A, CYC1, NCF1B, NCF1C, NCF4, NDUFA12, NDUFS2, NDUFS8, SHC1 and UQCR10 is chosen in a group comprising each of the 165 possible combinations.

In certain embodiments, the combination of 4 genes encoding a ROS producing (ROS) protein selected in a group comprising CYBA, CYB5A, CYC1, NCF1B, NCF1C, NCF4, NDUFA12, NDUFS2, NDUFS8, SHC1 and UQCR10 is chosen in a group comprising each of the 330 possible combinations.

In certain embodiments, the combination of 5 genes encoding a ROS producing (ROS) protein selected in a group comprising CYBA, CYB5A, CYC1, NCF1B, NCF1C, NCF4, NDUFA12, NDUFS2, NDUFS8, SHC1 and UQCR10 is chosen in a group comprising each of the 462 possible combinations.

In certain embodiments, the combination of 6 genes encoding a ROS producing (ROS) protein selected in a group comprising CYBA, CYB5A, CYC1, NCF1B, NCF1C, NCF4, NDUFA12, NDUFS2, NDUFS8, SHC1 and UQCR10 is chosen in a group comprising each of the 462 possible combinations.

In certain embodiments, the combination of 7 genes encoding a ROS producing (ROS) protein selected in a group comprising CYBA, CYB5A, CYC1, NCF1B, NCF1C, NCF4, NDUFA12, NDUFS2, NDUFS8, SHC1 and UQCR10 is chosen in a group comprising each of the 330 possible combinations.

In certain embodiments, the combination of 8 genes encoding a ROS producing (ROS) protein selected in a group comprising CYBA, CYB5A, CYC1, NCF1B, NCF1C, NCF4, NDUFA12, NDUFS2, NDUFS8, SHC1 and UQCR10 is chosen in a group comprising each of the 165 possible combinations.

In certain embodiments, the combination of 9 genes encoding a ROS producing (ROS) protein selected in a group comprising CYBA, CYB5A, CYC1, NCF1B, NCF1C, NCF4, NDUFA12, NDUFS2, NDUFS8, SHC1 and UQCR10 is chosen in a group comprising each of the 55 possible combinations.

In certain embodiments, the combination of 10 genes encoding a ROS producing (ROS) protein selected in a group comprising CYBA, CYB5A, CYC1, NCF1B, NCF1C, NCF4, NDUFA12, NDUFS2, NDUFS8, SHC1 and UQCR10 is chosen in a group comprising each of the 11 possible combinations.

In certain preferred embodiments, the expression level of each of the 11 genes encoding a ROS producing (ROS) protein consisting of CYBA, CYB5A, CYC1, NCF1B, NCF1C, NCF4, NDUFA12, NDUFS2, NDUFS8, SHC1 and UQCR10 is measured at step a).

In certain embodiments, the expression level of 16 genes encoding a ROS detoxifying (AOX) protein consisting of AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and/or the expression level of 11 genes encoding ROS producing (ROS) protein consisting of CYBA, CYB5A, CYC1, NCF4, NCF1B, NCF1C, NDUFA12, NDUFS2, NDUFS8, SHC1 and UQCR10, is measured at step a).

In some embodiments, the expression level of 16 genes encoding a ROS detoxifying (AOX) protein consisting of AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and the expression level of 11 genes encoding ROS producing (ROS) protein consisting of CYBA, CYB5A, CYC1, NCF4, NCF1B, NCF1C, NDUFA12, NDUFS2, NDUFS8, SHC1 and UQCR10, is measured at step a).

In certain embodiments, the expression level of at least 2 genes encoding either a ROS detoxifying (AOX) protein or a ROS producing (ROS) protein, the said genes being selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is measured in step a).

The different combinations from this embodiment also include redundancy of the combinations obtained from the groups taken separately.

In certain embodiments, the combination of 2 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 351 possible combinations.

In certain embodiments, the combination of 3 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 2925 possible combinations.

In certain embodiments, the combination of 4 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 17550 possible combinations.

In certain embodiments, the combination of 5 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 80730 possible combinations.

In certain embodiments, the combination of 6 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 296010 possible combinations.

In certain embodiments, the combination of 7 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 888030 possible combinations.

In certain embodiments, the combination of 8 genes selected in a group comprising of AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 2220075 possible combinations.

In certain embodiments, the combination of 9 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 4686825 possible combinations.

In certain embodiments, the combination of 10 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 8436285 possible combinations.

In certain embodiments, the combination of 11 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 13037895 possible combinations.

In certain embodiments, the combination of 12 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 17383860 possible combinations.

In certain embodiments, the combination of 13 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 20058300 possible combinations.

In certain embodiments, the combination of 14 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 20058300 possible combinations.

In certain embodiments, the combination of 15 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 17383860 possible combinations.

In certain embodiments, the combination of 16 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 13037895 possible combinations.

In certain embodiments, the combination of 17 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 8436285 possible combinations.

In certain embodiments, the combination of 18 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 4686825 possible combinations.

In certain embodiments, the combination of 19 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 2220075 possible combinations.

In certain embodiments, the combination of 20 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 888030 possible combinations.

In certain embodiments, the combination of 21 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 296010 possible combinations.

In certain embodiments, the combination of 22 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 80730 possible combinations.

In certain embodiments, the combination of 23 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 17550 possible combinations.

In certain embodiments, the combination of 24 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 2925 possible combinations.

In certain embodiments, the combination of 25 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 351 possible combinations.

In certain embodiments, the combination of 26 genes selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is chosen in a group comprising each of the 27 possible combinations.

In certain preferred embodiments, the expression level of each of the 27 genes consisting of AKR1B1, ARNT, CAT, CBR1, DHCR24, EGLN1, GLRX2, HIF1A, MGST1, MSRB1, PRDX6, SLC7A11, SOD1, SRXN1, TALDO1, TXN, CYBA, CYB5A, CYC1, NCF1B, NCF1C, NCF4, NDUFA12, NDUFS2, NDUFS8, SHC1 and UQCR10 is measured in step a).

In some embodiments, the individual having MM may originate from the general population of MM individuals, from early stage MM individuals, from intermediary stage MM individuals, from late stage MM individuals.

In some other embodiments, the individual having MM may originate from MM individuals not undergoing therapeutic treatment, from MM individuals not undergoing therapeutic treatment but having experienced at least one previous therapeutic treatment, from MM individuals undergoing therapeutic treatment, from MM individuals experiencing a refractory/relapsing MM, and a combination thereof.

Within the scope of the present invention, a "biological sample" refers to a biological sample obtained, reached, collected or isolated from an individual, in vivo or in situ. Such samples may be, but not limited to, organs, tissues, fractions and cells isolated from an individual. For example, suitable biological samples include but are not limited to a cell culture, a cell line, a tissue biopsy such as a bone marrow aspirate, a biological fluid such as a blood, pleural effusion or a serum sample, and the like.

In certain embodiments, the preferred biological sample includes but is not limited to a blood sample, a tissue biopsy, including a bone marrow aspirate.

In some embodiments, the biological sample may be a crude sample.

In some other embodiments, the biological sample may be purified to various degrees prior to storage, processing, or measurement.

The expression level of the defined set of genes may be measured by the mean of any technique used in the field.

In some embodiments, the expression level of a gene of interest may be measured through the quantification of the level of mRNA expression.

In some embodiments, the level of mRNA expression for each of the genes of interest may be performed using the well-known techniques available in the state of the art.

Illustratively, mRNA may be extracted, for example using lytic enzymes or chemical solutions or extracted by commercially available nucleic-acid-binding resins following the manufacturer's instructions. Extracted mRNA may be subsequently detected by hybridization, such as Northern blot, and/or amplification, such as quantitative or semi-quantitative RT-PCR. Other methods of amplification include ligase chain reaction (LCR), transcription-mediated amplification (TMA), strand displacement amplification (SDA) and nucleic acid sequence based amplification (NASBA).

In some embodiments, the level of mRNA expression for each of the genes of interest may be measured by the mean of quantification of the cDNA synthesized from said mRNA, as a template, by one reverse transcriptase.

Methods for determining the quantity of mRNA by microarrays or by RNA sequencing may also be used.

In certain embodiments, complexes between the double-stranded nucleic acids resulting from amplification and fluorescent SYBR® molecules may be obtained and then the fluorescence signal generated by the SYBR® molecules complexed with the said amplified nucleic acids may be measured.

Identification of suitable primers that are specific for each of the genes mRNA consists of a routine work for the one skilled in the art.

In certain embodiments, detection by hybridization may be performed with a detectable label, such as fluorescent probes, radioactive probes, enzymatic reactions or other ligands (e.g. avidin/biotin).

The expression level for each combination of genes of interest may be associated with a score value.

Illustratively, following the measurement of the expression level of at least 2 or more genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN and/or the expression level of at least 2 or more genes a encoding a ROS producing (ROS) protein group comprising CYBA, CYB5A, CYC1, NCF1B, NCF1C, NCF4, NDUFA12, NDUFS2, NDUFS8, SHC1 and UQCR10, in a biological sample obtained from an individual having MM (step a) of the method), the computation of a score value may be performed by a method comprising the following steps:

i) providing a standardized expression level (L) for each of the considered gene, obtained by any suitable method, as described above;
ii) calculating the score value with the following formula:

$$\text{Score} = \sum_{i=1}^{n} \beta i \times Li \quad \text{[Math 1]}$$

wherein:

n represents the number of genes which expression level is measured; n can either be comprised:
from 2 to 16 (genes encoding a ROS detoxifying (AOX) protein); or
from 2 to 11 (genes encoding a ROS producing (ROS) protein); or
from 2 to 27 when the combination of the genes encoding a ROS detoxifying (AOX) protein and the genes encoding a ROS producing (ROS) protein is considered;
βi represents the regression β coefficient reference value for a given gene.

In some embodiments, the standardized expression level (L) is obtained by measuring the quantity of mRNA by the means of a microarray, in particular an Affymetrix™ microarray.

In some embodiments, individuals having MM may be classified according to increased or decreased AOX and/or increased or decreased ROS risk signatures and subsequently attributed in one prognostic group using Maxstat cut points for the demarcation of good and bad prognosis patients.

In some embodiments, a score value below said reference value is indicative of a good prognosis status.

In some embodiments, a score value equal or above said reference value is indicative of a bad prognosis status.

In certain embodiments, the individual having a bad prognosis status is likely to display a bad outcome.

The regression β coefficient reference value may be easily determined by the skilled man in the art for each gene or protein using the well-known statistical Cox model, which is based on a modelling approach to analyse survival data. The purpose of the model is to simultaneously explore the effects of several variables on survival. When it is used to analyse the survival of patients in a clinical trial, the model allows isolating the effects of the treatment from the effects of other variables.

The Cox model may also be referred as to proportional hazards regression analysis. In particular, this model is a regression analysis of the survival times (or more specifically, the so-called hazard function) with respect to defined variables. The hazard function is the probability that an individual will experience an event, e.g. death, within a small time interval, given that the individual has survived up to the beginning of the interval. It can therefore be interpreted as the risk of dying at time t. The quantity h0 (t) is the baseline or underlying hazard function and corresponds to the probability of dying (or reaching an event) when all the defined variables are zero. The baseline hazard function is analogous to the intercept in ordinary regression (since exp0=1). The regression coefficient β gives the proportional change that can be expected in the hazard, related to changes in the defined variables. The coefficient β is estimated by a statistical method called maximum likelihood. In survival analysis, the hazard ratio (HR) (Hazard Ratio=exp(β)) is the ratio of the hazard rates corresponding to the conditions described by two sets of defined variables. For example, in a drug study, the treated population may die at twice the rate per unit time as the control population. The hazard ratio would be 2, indicating higher hazard of death from the treatment.

Another aspect of the invention relates to the use of the expression level of at least 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and/or the expression level of at least 2 genes encoding ROS producing (ROS) protein selected in a group comprising CYBA, CYB5A, CYC1, NCF1B, NCF1C, NCF4, NDUFA12, NDUFS2, NDUFS8, SHC1 and UQCR10, to calculate an AOX score value and/or a ROS score value representing a biomarker for predicting the outcome of an individual having a multiple myeloma.

In some embodiments, the score value may be calculated with the following formula:

$$\text{Score} = \sum_{i=1}^{n} \beta i \times Li \quad \text{[Math 1]}$$

wherein n, βi and Li represent the same integer as previously defined above.

Another aspect of the invention further relates to a method for in vitro predicting the outcome of an individual having a multiple myeloma and the treatment of said individual, comprising the steps of:
a) measuring the expression level of at least 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN and/or the expression level of at least 2 genes encoding ROS producing (ROS) protein selected in a group comprising CYBA, CYB5A, CYC1, NCF1B, NCF1C, NCF4, NDUFA12, NDUFS2, NDUFS8, SHC1 and UQCR10, in a biological sample obtained from said individual;
b) calculating an AOX score value and/or a ROS score value from the said respective expression level(s) obtained at step a);
c) classifying the said individual as having a good prognosis status or a bad prognosis status, by comparing the score value obtained at step b) with a reference score value; and
d) administering the said individual with an anti-cancer treatment.

2/Identification of Multiple Myeloma Individuals that are Likely to Respond to a Therapeutic Treatment Another aspect of the invention relates to a method for in vitro predicting the likelihood of an individual having a multiple myeloma to respond to a therapeutic anti-MM treatment, comprising the steps of:
a) measuring the expression level of at least 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and the expression level of at least 2 genes encoding ROS producing (ROS) protein selected in a group comprising CYBA, CYB5A, CYC1, NCF1B, NCF1C, NCF4, NDUFA12, NDUFS2, NDUFS8, SHC1 and UQCR10, in a biological sample obtained from an individual having a multiple myeloma;

b) calculating a AOX score value and a ROS score value from the said respective expression levels obtained at step a);

c) classifying the said individual as being a responsive individual or a non-responsive individual, by comparing each score value obtained at step b) with a reference score value.

Within the scope of the invention, the expression "likelihood to respond to" is meant to intend that the MM individual may be subjected to stabilization, an alleviating, a curing or a reduction of the progression of the symptoms or the disease itself.

Within the scope of the present invention, it has to be understood that the expression level of any combination of 2, 3, 4, 5, 6, 7, 8, 9, 10, 11, 12, 13, 14, 15 and 16 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN and the expression level of any combination of 2, 3, 4, 5, 6, 7, 8, 9, 10 and 11 genes encoding a ROS producing (ROS) protein selected in a group comprising CYBA, CYB5A, CYC1, NCF1B, NCF1C, NCF4, NDUFA12, NDUFS2, NDUFS8, SHC1 and UQCR10 is of special interest. Each possible combination corresponding to each list separately is disclosed above.

In some embodiments, the score value may be calculated with the following formula:

$$\text{Score} = \sum_{i=1}^{n} \beta i \times Li \qquad \text{[Math 1]}$$

wherein n, βi and Li represent the same integer as previously defined above.

In some embodiments, a responsive individual refers to an individual having a score value lower than or equal to a predetermined reference value (PRV).

In some embodiments, a non-responsive individual refers to an individual having a score value higher than a predetermined reference value (PRV).

In certain embodiments, a AOX score value and a ROS score value below said reference values are indicative of a likelihood of said individual having a multiple myeloma to respond to a therapeutic anti-MM treatment.

In certain preferred embodiments, the expression level of each of the 16 genes encoding a ROS detoxifying (AOX) protein consisting of AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and the expression level of 11 genes encoding ROS producing (ROS) protein consisting of CYBA, CYB5A, CYC1, NCF1B, NCF1C, NCF4, NDUFA12, NDUFS2, NDUFS8, SHC1 and UQCR10, is measured at step a).

In some embodiments, the therapeutic treatment comprises at least one anticancer compound, at least one bisphosphonate, radiation, surgery, stem cell transplant, plasmapheresis and a combination thereof.

In certain embodiments, the responsive individual is likely to respond to the said therapeutic treatment comprising an anticancer compound.

In certain embodiments, the anticancer compound is selected in a group comprising bendamustine, bortezomib, carfilzomib, cyclophosphamide, daratumumab, dexamethasone, doxorubicin, elotuzumab, etoposide, ixazomib, liposomal doxorubicin, melphalan, panobinostat, prednisone, vincristine and a combination thereof.

In certain embodiments, the anticancer compound is selected in a group comprising bortezomib and melphalan.

In certain embodiments, the MM individual may be chosen in a group comprising MM individual general population of MM individuals, from early stage MM individuals, from intermediary stage MM individuals, from late stage MM individuals, from MM individuals not undergoing therapeutic treatment, from MM individuals not undergoing therapeutic treatment but having experienced at least one previous therapeutic treatment, from MM individuals undergoing therapeutic treatment, from MM individuals experiencing a MM relapse, and a combination thereof.

Another aspect of the invention relates to the use of the expression level of at least 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and the expression level of at least 2 genes encoding ROS producing (ROS) protein selected in a group comprising CYBA, CYB5A, CYC1, NCF1B, NCF1C, NCF4, NDUFA12, NDUFS2, NDUFS8, SHC1 and UQCR10, to calculate an AOX score value and a ROS score value representing a biomarker for predicting the likelihood of an individual having a multiple myeloma to respond to a therapeutic anti-MM treatment.

In some embodiments, the score value may be calculated with the following formula:

$$\text{Score} = \sum_{i=1}^{n} \beta i \times Li \qquad \text{[Math 1]}$$

wherein n, βi and Li represent the same integer as previously defined above.

In certain embodiments, an individual having a multiple myeloma that is likely to respond to a therapeutic anti-MM treatment may be an individual having a low AOX score value and/or a low ROS score value.

In certain embodiments, an individual having a multiple myeloma that is not likely to respond to a therapeutic anti-MM treatment may be an individual having a high AOX score value and/or a high ROS score value.

Another aspect of the invention relates to a method for in vitro predicting the likelihood of an individual having a multiple myeloma to respond to a therapeutic anti-MM treatment and for treating a responsive individual, comprising the steps of:

a) measuring the expression level of at least 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and the expression level of at least 2 genes encoding ROS producing (ROS) protein selected in a group comprising CYBA, CYB5A, CYC1, NCF1B, NCF1C, NCF4, NDUFA12, NDUFS2, NDUFS8, SHC1 and UQCR10, in a biological sample obtained from an individual having a multiple myeloma;

b) calculating a AOX score value and a ROS score value from the said respective expression levels obtained at step a);

c) classifying the said individual as being a responsive individual or a non-responsive individual, by comparing each score value obtained at step b) with a reference score value;

d) administering to the said responsive individual an anti-MM treatment.

In some embodiments, the anti-MM treatment comprises the administration of an anticancer compound, in particular selected in a group comprising bortezomib and melphalan.

3/Determination of the Aggressiveness of a Multiple Myeloma Disease and Monitoring of MM Individual During a Therapeutic Treatment Another aspect of the invention relates to the use of the expression level of at least 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and/or the expression level of at least 2 genes encoding ROS producing (ROS) protein selected in a group comprising CYBA, CYB5A, CYC1, NCF1B, NCF1C, NCF4, NDUFA12, NDUFS2, NDUFS8, SHC1 and UQCR10, to calculate an AOX score value and/or a ROS score value representing a biomarker for assessing the aggressiveness of a multiple myeloma disease in an individual having a multiple myeloma.

Within the scope of the invention, the "aggressiveness of a MM disease" is intended to refer to the degree of malignancy of the MM disease by the mean of one or more parameters, e.g. the velocity of multiplication of the malignant cells, the velocity of the spreading of the malignant cells in the bone marrow and the resistance to therapeutic treatments.

It is understood that slow velocity of multiplication of the malignant cells, and/or slow velocity of the spreading of the malignant cells in the bone marrow would be indicative of a non-aggressive or a poorly aggressive MM; whereas high velocity of multiplication of the malignant cells, and/or high velocity of the spreading of the malignant cells in the bone marrow would be indicative of an aggressive MM.

An aggressive MM disease may also be associated with poor survival prognosis.

In some embodiments, the score value may be calculated with the following formula:

$$\text{Score} = \sum_{i=1}^{n} \beta i \times Li \quad \text{[Math 1]}$$

wherein n, βi and Li represent the same integer as previously defined above.

In certain embodiments, an individual having a non-aggressive or a poorly aggressive multiple myeloma may be an individual having a low AOX score value and/or a low ROS score value.

In certain embodiments, an individual having an aggressive multiple myeloma may be an individual having a high AOX score value and/or a high ROS score value.

4/Anticancer Compound and Therapeutic Treatment

Another aspect of the invention relates to an anticancer compound or a combination thereof for use in treating multiple myeloma in an individual in need thereof, wherein said individual is classified as being a responsive individual by the method previously described.

In some other aspects, the invention also relates to an anticancer compound or a combination thereof for use in treating multiple myeloma in an individual in need thereof, wherein said individual is classified as being a responsive individual by a method comprising the steps of:

a) measuring the expression level of at least 2 genes encoding a ROS detoxifying (AOX) protein selected in a group comprising AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and the expression level of at least 2 genes encoding ROS producing (ROS) protein selected in a group comprising CYBA, CYB5A, CYC1, NCF1B, NCF1C, NCF4, NDUFA12, NDUFS2, NDUFS8, SHC1 and UQCR10, in a biological sample obtained from an individual having a multiple myeloma;

b) calculating a AOX score value and a ROS score value from the said respective expression levels obtained at step a);

c) classifying the said individual as being a responsive individual or a non-responsive individual, by comparing each score value obtained at step b) with a reference score value.

In certain embodiments, individual classified as being a responsive individual may be an individual having a low AOX score value and/or a low ROS score value.

In certain embodiments, an individual classified as being a non-responsive individual may be an individual having a high AOX score value and/or a high ROS score value.

In some embodiments, anticancer compounds may include a chemo drug, in particular selected in a group comprising melphalan, vincristine, cyclophosphamide, etoposide, doxorubicin, liposomal doxorubicin and bendamustine.

In some embodiments, anticancer compounds may include a corticosteroid, in particular selected in a group comprising dexamethasone and prednisone.

In some embodiments, anticancer compounds may include a proteasome inhibitor, in particular selected in a group comprising bortezomib, carfilzomib and ixazomib.

In some embodiments, anticancer compounds may include a histone deacetylase (HDAC) inhibitor, in particular panobinostat.

In some embodiments, anticancer compounds may include a monoclonal antibody, in particular selected in a group comprising daratumumab and elotuzumab.

In some embodiments, the anticancer compound may also be combined in a therapeutic treatment to one bisphosphonate, radiation, surgery, stem cell transplant, plasmapheresis or a combination thereof.

In certain embodiments, the anticancer compound is selected in a group comprising bendamustine, bortezomib, carfilzomib, cyclophosphamide, daratumumab, dexamethasone, doxorubicin, elotuzumab, etoposide, ixazomib, liposomal doxorubicin, melphalan, panobinostat, prednisone, vincristine and a combination thereof.

In certain embodiments, the anticancer compound is selected in a group comprising bortezomib and melphalan.

EXAMPLES

1/Materials and Methods 1.1/Gene Expression Profile Data from Multiple Myeloma Cells and Human Myeloma Cell Lines Two GEP data have been considered to investigate the redox status in normal plasma cells and MM cells. GEP data from Total therapy (TT) 2 trial cohort enrolling human samples of MM patients with overt MM disease requiring therapy (n=345) were used as training cohort (Accession number GSE2658). These patients were treated with total therapy 2 protocol (UAMS-TT2 cohort) at the University of Arkansas for Medical Sciences (UAMS, Little Rock, USA) (Barlogie et al., 2006). In addition, TT2 cohort enrolls BMPCs from healthy donors (BMPC, n=22), Monoclonal gammopathy of Undermined Significance (MGUS=44) and samples from patients with Smoldering Myeloma (SMMC=12). GEP data from Heidelberg (Germany)-Montpellier (France) (HM) cohort enrolling 206 untreated MM patients were considered as validation cohort in addition of 5 BMPCs samples (accession number E-MTAB-362). These patients were treated according to the GMMG-HD3 trial (Goldschmidt et al., 2003).

XG-1, XG-2, XG-3, XG-4, XG-5, XG-6, XG-7, XG-10, XG-11, XG-12, XG-13, XG-14, XG-16, XG-19, XG-20, and XG-21 HMCLs were obtained as previously described (Tarte et al., 1999; Moreaux et al., 2011). JJN3 was kindly provided by Dr. Ivan Van Riet (Academic Hospital, Free University Brussels, Bruxelles, Belgium), JIM3 by Dr. Ian MacLennan (University of Birmingham, Birmingham, UK), and MMIS by Dr. Steven Rosen (Northwestern University, Chicago, IL). AMO1, LP1, L363, U266, OPM2, and SKMM2 were from DSMZ and RPMI8226 from American Type Culture Collection. Gene expression profiling data from HMCLs have been deposited in the ArrayExpress public database under accession numbers E-TABM-937 and E-TABM-1088.

1.2/HMCLs Culture and Treatment

The HMCLs XG-6, XG-19, XG-20, XG24, JJN3, AMO1, LP1, L363, OPM2 and RPMI8226 were grown in RPMI-1640 supplemented with 10% FBS. XG-6, XG-19, XG-20, XG-24, and LP1 media was supplemented with 2 ng/mL recombinant IL-6. Cells were plated in 96-well plate in 200 µL complete medium. After 24h, cells were treated with increasing concentrations of Melphalan (European Pharmacopeia Reference-Standards, France) or Bortezomib (Axon, Medchem, France) and at day 4 post treatment, the viable cells were assessed using Cell Titer Glo assay (Promega, Madison, WI). The IC50 at 96h were determined using GraphPad Prism software.

1.3/AOX/ROS Risk Signatures and Patients Stratification

Using a univariate Cox Model, AOX and ROS genes whose expression in MMCs could predict for patients' Event Free Survival (EFS) were identified. Monitoring data of the first EFS rather than overall survival (OS) was selected because patients received a homogeneous treatment until the first relapse, thereafter, several drug combinations were applied. The expression of the prognostic genes was summed within one parameter, i.e. "AOX risk signature" or "ROS risk signature", by computing the mean of their standardized Affymetrix™ signals weighted by their Cox Beta Coefficient. Patients were then ranked according to increased AOX or ROS risk signatures and split into different prognostic groups using Maxstat cut points for the demarcation of good and bad prognosis patients.

1.4/Data Analysis

Gene expression analysis, SAM analysis, survival curves and figures editing were performed using the free datamining web site, genomicscape.com (Kassambara et al., 2015). Multivariate analysis was performed using the Cox proportional hazards model and were performed using R software (r-project.org). Gene set enrichment analysis was performed using the Reactome and Pathway Studio softwares.

2/Results 2.1/AOX and ROS Risk Signatures in Multiple Myeloma 2.2.1/AOX Score (AOX Risk Signature)

Using a Cox univariate analysis, the expression of 16 genes among a consensus list of 53 genes encoding for and redox proteins was associated to bad prognosis for EFS in patients of the TT2 training cohort. Remarkably, no AOX genes were associated to good prognosis (see Table 1 below).

TABLE 1

The prognostic value of the expression of each of the 16 Antioxidant genes for predicting the EFS of the untreated patients of the TT2 cohort. Data are the beta coefficients, the hazard ratios (HR) and p-values of the Cox model.

| Name | Probe sets | Beta Coefficient | HR | p-value |
|---|---|---|---|---|
| GLRX2 | 219933_at | 0.27 | 1.3 | 0.000067 |
| EGLN1 | 223046_at | 0.21 | 1.2 | 0.0048 |
| PRDX6 | 200844_s_at | 0.19 | 1.2 | 0.013 |
| SRXN1 | 225252_at | 0.18 | 1.2 | 0.013 |
| TALDO1 | 201463_s_at | 0.18 | 1.2 | 0.018 |
| CBR1 | 209213_at | 0.17 | 1.2 | 0.0028 |
| HIF1A ß | 200989_at | 0.17 | 1.2 | 0.0094 |
| SOD1 | 200642_at | 0.16 | 1.2 | 0.027 |
| DHCR24 | 200862_at | 0.15 | 1.2 | 0.027 |
| MSRB1 | 217977_at | 0.15 | 1.2 | 0.033 |
| AKR1B1 | 201272_at | 0.14 | 1.2 | 0.049 |
| CAT | 201432_at | 0.14 | 1.2 | 0.045 |
| TXN | 208864_s_at | 0.14 | 1.2 | 0.039 |
| MGST1 | 224918_x_at | 0.13 | 1.1 | 0.029 |
| SLC7A11 | 217678_at | 0.13 | 1.1 | 0.042 |
| ARNT | 231016_s_at | 0.12 | 1.1 | 0.037 |

The prognostic genes include major frontline actors of the antioxidants response involving SOD1 and CAT, genes encoding for several enzymes involved in the interplay of protein oxidation and reduction MSRB1, SRXN1, PRDX6, and TXN, GLRX2, the cysteine transporter SLC7A11 and mitochondrial GST1 in addition to members of HIF1A pathway (HIF1A, EGLN and ARNT). Their expression was summed within an AOX risk signature and using a Max stat designed cut point, patients were split into 2 distinct groups with low and high AOX risk signatures (FIG. 1).

Figure 3:
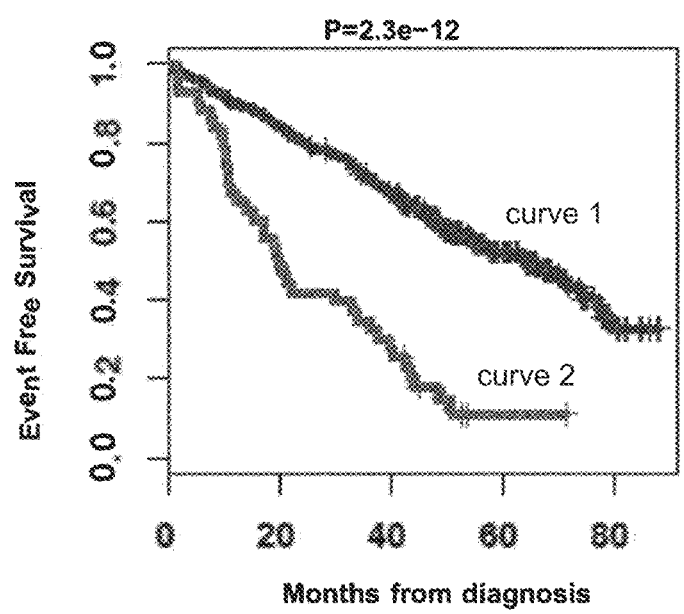
FIG. 3 is a plot illustrating the event free survival (EFS) Kaplan-Meier curves of the AOX signature groups from patients of the TT2 cohort. Curve 1 represents the patients with a low AOX risk signature, N=302 (87.5%) and curve 2 represents the patients with a high AOX risk signature, N=43 (12.5%).
Figure 4:
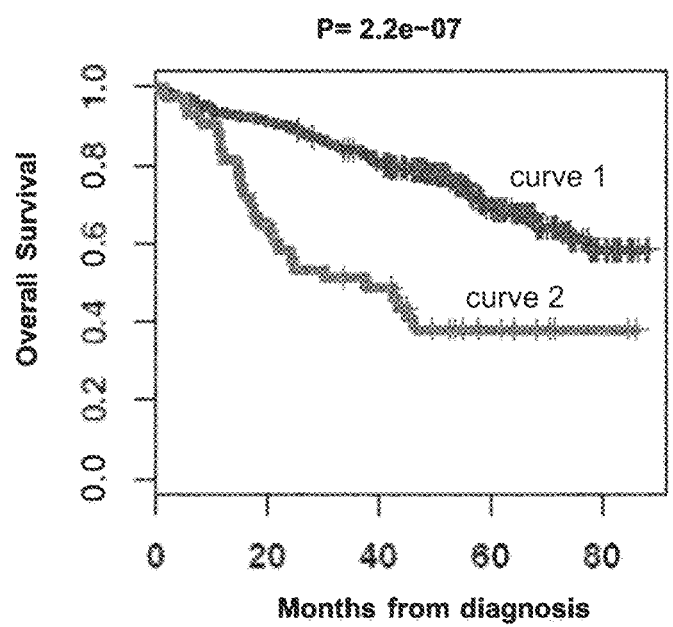
FIG. 4 is a plot illustrating the overall survival (OS) Kaplan-Meier curves of the AOX signature groups from patients of the TT2 cohort. Curve 1 represents the patients with a low AOX risk signature, N=302 (87.5%) and curve 2 represents the patients with a high AOX risk signature, N=43 (12.5%).

Survival curves showed a better prognosis for patients with low AOX risk signature (87.5% of TT2 patients, median of EFS 63.7 months and a non-reached median for OS) as compared to those with high AOX signature (12.5% of patients, median of EFS 19.6 months; Median of OS 37.7 months) (p=2.3×10$^{-12}$, p=2. 2×10$^{-7}$) (FIG. 3 and FIG. 4).

Figure 7:
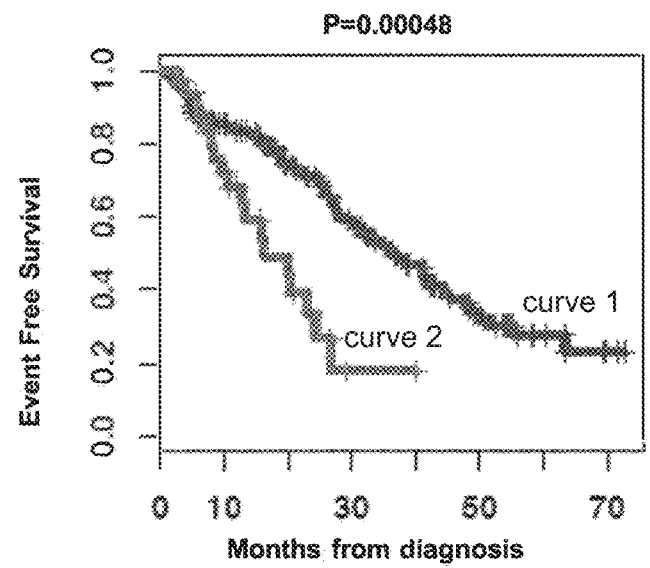
FIG. 7 is a plot illustrating the EFS Kaplan-Meier curves of the AOX signature groups in the HM cohort of MM patients. Curve 1 represents the patients with a low AOX risk signature, N=173 (84%), and curve 2 represents the patients with a high AOX risk signature, N=33 (16%).
Figure 8:
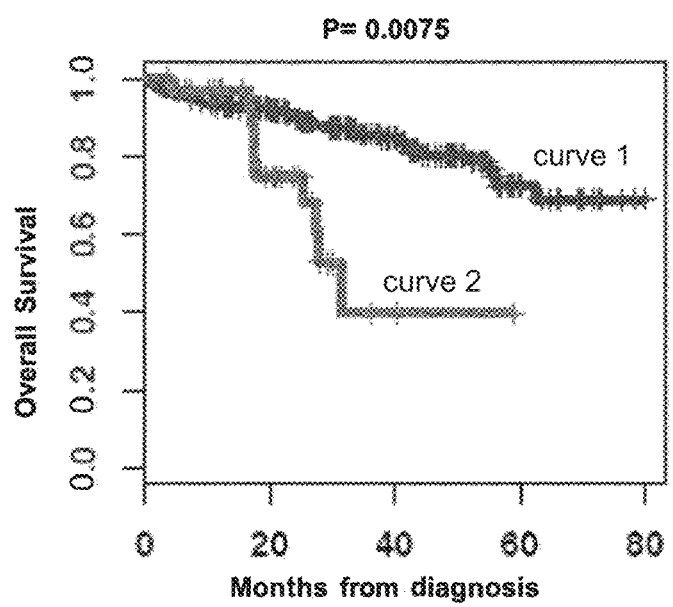
FIG. 8 is a plot illustrating the OS Kaplan-Meier curves of the AOX signature groups in the HM cohort of MM patients. Curve 1 represents the patients with a low AOX risk signature, N=173 (84%), and curve 2 represents the patients with a high AOX risk signature, N=33 (16%).

To validate the relevance of the AOX risk signature in the prediction of EFS and OS, the HM validation cohort was assayed (FIG. 7 and FIG. 8). The data showed that 16% of patients have a high AOX signature and display a gloomy prognosis with 16.1 and 31.3 months of median EFS (FIG. 7) and OS (FIG. 8), respectively as compared to 84% of patients bears low AOX risk signature with 36.5 months as median EFS and a non-reached OS median (p=0.00075, p=0.00048).

2.2.2/ROS Score (ROS Risk Signature)

Intriguingly, 11 out of 106 ROS genes were found prognostic for EFS in patients of the TT2 cohort (see Table 2 below).

TABLE 2

The prognostic value of the expression of each of the 11 ROS producing genes for predicting the EFS of the untreated patients of the TT2. Data are the beta coefficients, the hazard ratios (HR) and p-values of the Cox model.

| Name | Probe sets | Beta Coefficient | HR | p-value |
|---|---|---|---|---|
| NDUFS2 | 201966_at | 0.29 | 1.3 | 0.000082 |
| CYB5A | 209366_x_at | 0.26 | 1.3 | 0.00025 |
| UQCR10 | 218190_s_at | 0.22 | 1.3 | 0.0056 |
| CYC1 | 201066_at | 0.2 | 1.2 | 0.0076 |
| NDUFA12 | 223244_s_at | 0.18 | 1.2 | 0.015 |
| SHC1 | 214853_s_at | 0.14 | 1.2 | 0.05 |
| NCF4 | 2051 47_x_at | −0.17 | 0.84 | 0.023 |
| NCF1B | 204961_s_at | −0.19 | 0.83 | 0.025 |
| NCF1C | 214084_x_at | −0.21 | 0.81 | 0.011 |
| NDUFS8 | 203190_at | −0.22 | 0.81 | 0.0076 |
| CYBA | 2o3o2s_s_at | −0.26 | 0.77 | 0.0015 |

Six genes were associated to bad prognosis and include NADH Ubiquinone Oxidoreductase (NDUFS2) of the mitochondrial complex I, Ubiquinol-cytochrome C Reductase subunit 4 (UQCR10) and subunit 10 (CYC1) of the mitochondrial Complex III, the microsomal Cytochrome B5 (CYB5A) and Src Homology 2 Domain-Containing Transforming Protein 1 (SHC1, p66Shc).

Five genes were associated with a good prognosis and include 4 genes encoding for NOX subunits, CYBA ($p22^{phox}$), NCF1 ($p47^{phox}$), NCF4 ($p40^{phox}$) and NCF1C (Table 2).

Figure 2:
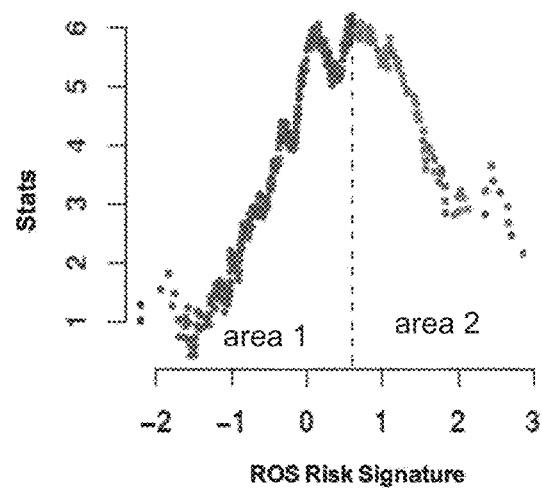
FIG. 2 is a diagram representing patients of the TT2 cohort ranked according to increasing ROS risk signatures. Maxstat function was used to identify the 0.6 cut off points (dashed line) and to further distinguish patients with a low (area 1) from patients with a high (area 2) ROS risk signature.

The ROS risk signature integrating the expression and beta coefficient of ROS prognostic genes was calculated and patients were split into groups using Max stat algorithms (FIG. 2).

Figure 5:
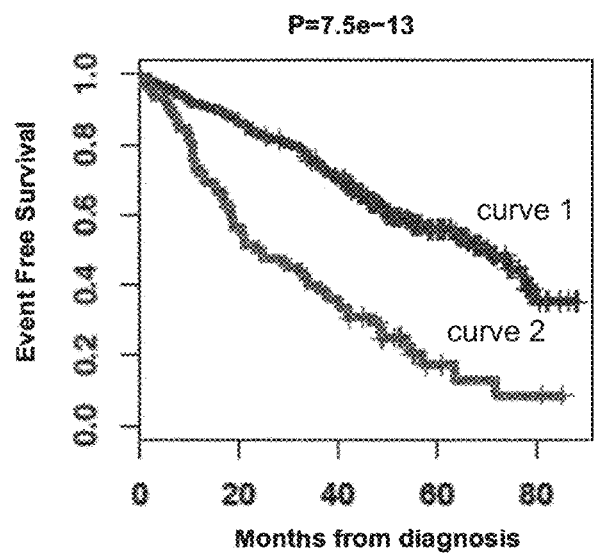
FIG. 5 is a plot illustrating the EFS Kaplan-Meier curves of the ROS signature groups in the TT2 cohort of MM patients. Curve 1 represents the patients with a low ROS risk signature, N=267 (77.4%) and curve 2 represents the patients with a high ROS risk signature, N=78 (22.6%).
Figure 6:
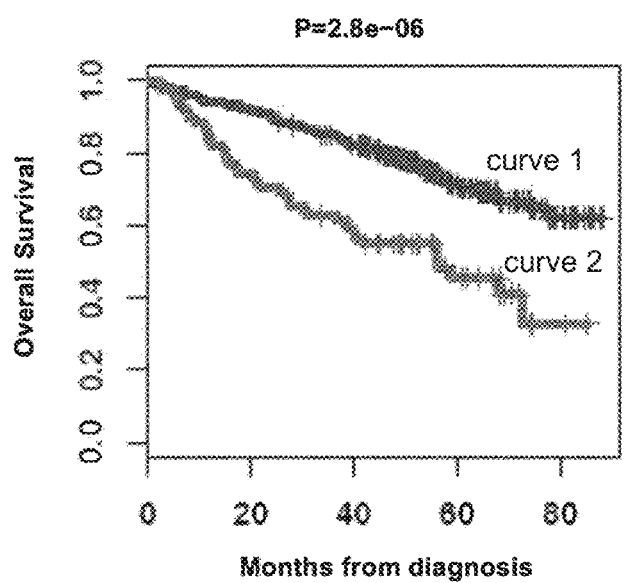
FIG. 6 is a plot illustrating the OS Kaplan-Meier curves of the ROS signature groups in the TT2 cohort of MM patients. Curve 1 represents the patients with a low ROS risk signature, N=267 (77.4%) and curve 2 represents the patients with a high ROS risk signature, N=78 (22.6%).

Kaplan Meier curves showed that 77.4% of patients with low ROS risk signature have a median of 69.6 months for EFS and non-reached median for OS ($p=7.5\times10^{-13}$, $p=2.8\times10^{-6}$) as compared to 22.6% of TT2 patients with high ROS risk signature where the medians for EFS (FIG. 5) and OS (FIG. 6) are 24 months and 56.3 months, respectively ($p=7.5\times10^{-13}$; $p=2.8\times10^{-6}$).

Figure 9:
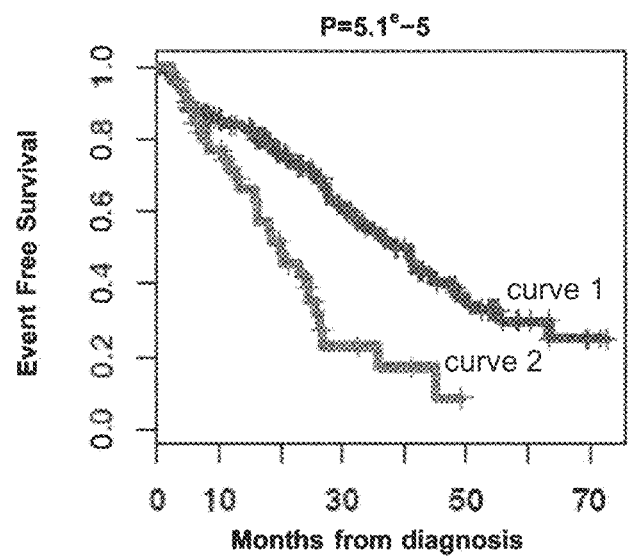
FIG. 9 is a plot illustrating the EFS Kaplan-Meier curves of the ROS signature groups in the HM cohort of MM patients. Curve 1 represents the patients with a low ROS risk signature, N=159 (77.2%) and curve 2 represents the patients with a high ROS risk signature, N=47 (22.8%).
Figure 10:
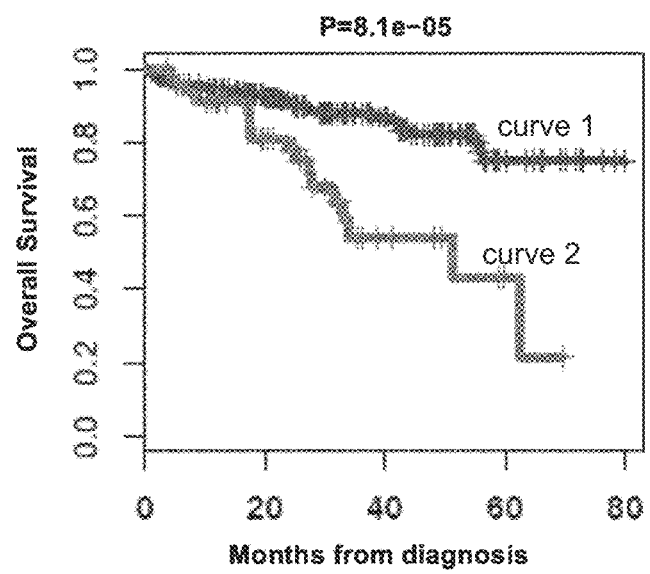
FIG. 10 is a plot illustrating the OS Kaplan-Meier curves of the ROS signature groups in the HM cohort of MM patients. Curve 1 represents the patients with a low ROS risk signature, N=159 (77.2%) and curve 2 represents the patients with a high ROS risk signature, N=47 (22.8%).

Similarly, using the cut off designed with the TT2 cohort; patients of the independent HM cohort were divided into low and high ROS Risk signature groups comprising 77.2% and 22.8% of patients, respectively. The median EFS of patients of the high ROS risk signature group was 2-fold shorter than that of the low ROS Risk signature group ($p=5.1\times10^{-5}$, $p=8.1\times10^{-5}$) (FIG. 9 and FIG. 10).

Figure 11:
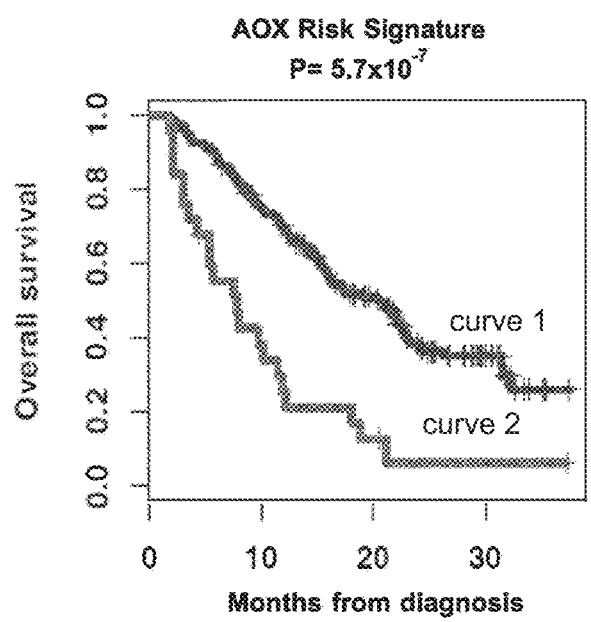
FIG. 11 is a plot illustrating the OS Kaplan-Meier curves of the AOX risk group from patients from the Mulligan cohort of MM patients (n=188).
Figure 12:
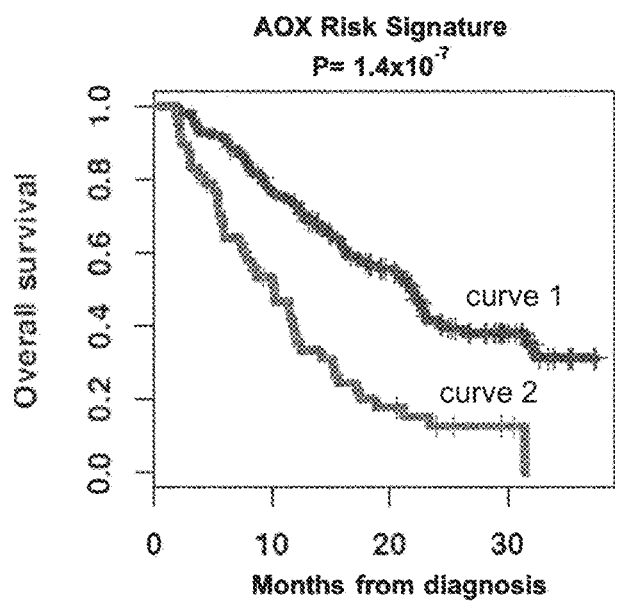
FIG. 12 is a plot illustrating the Kaplan-Meier curves of the OS of the ROS risk group from patients from the Mulligan cohort of MM patients (n=188).

Similar findings have been reported when a third MM cohort was assayed (Mulligan cohort, n=188) further underlying the robustness of both AOX and ROS risk signatures (Mulligan et al., 2007)(FIG. 11 and FIG. 12).

2.2/Redox Profile of MM Patients

Figure 13:
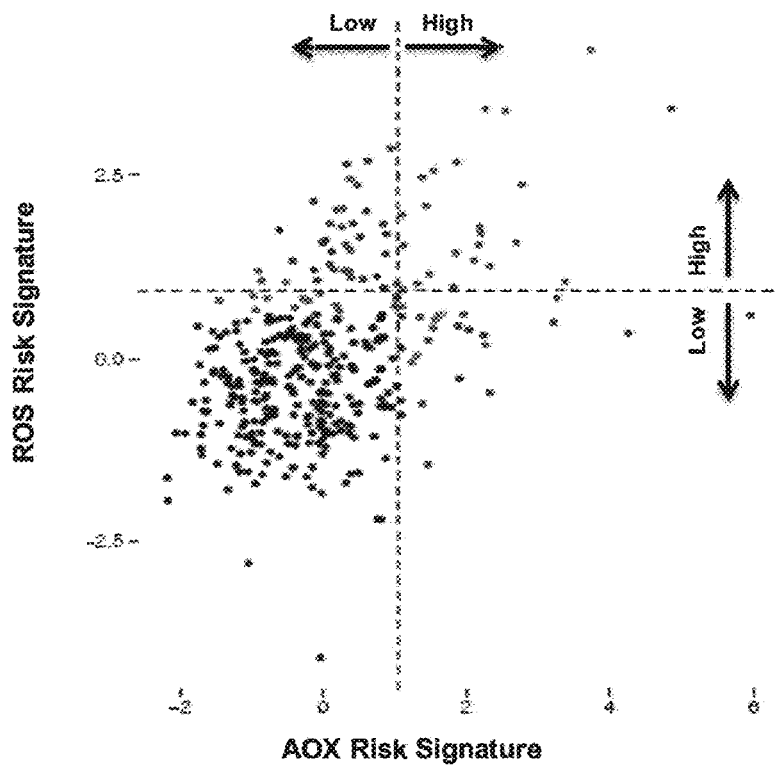
FIG. 13 is a scatter plot diagram of AOX and ROS risk signature for patients of the TT2 cohort (N=345).

To gain better insight on the relation between AOX and ROS risk signatures, AOX and ROS risk signatures have been depicted in a single scatter plot diagram (FIG. 13). This diagram highlighted the heterogeneity among patient's redox status and split patients into 3 groups, i.e. (1) high AOX and high ROS (high AOX/ROS), (2) either low AOX and high ROX, or high AOX and low ROS,—and (3) low AOX and low ROS (low AOX/ROS)-risk signatures according to AOX and ROS risk signatures cut points.

Figure 14:
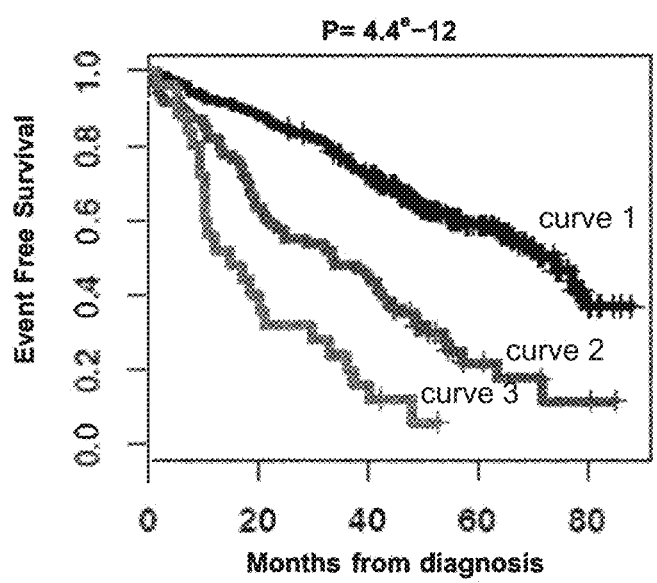
FIG. 14 is a plot illustrating the Kaplan-Meier curves of the EFS of the AOX and ROS signature groups of patients of the TT2 cohort (N=345) corresponding to the scatterplot in FIG. 13. Curve 1 represents the patients with a low AOX and a low ROS risk signature, N=249 (72.2%), curve 2 represents either the patients with a high AOX and a low ROS risk signature or with a low AOX and a high ROS risk signature, N=71 (20.6%), and curve 3 represents the patients with a high AOX and a high ROS risk signature, N=25 (7.2%).
Figure 15:
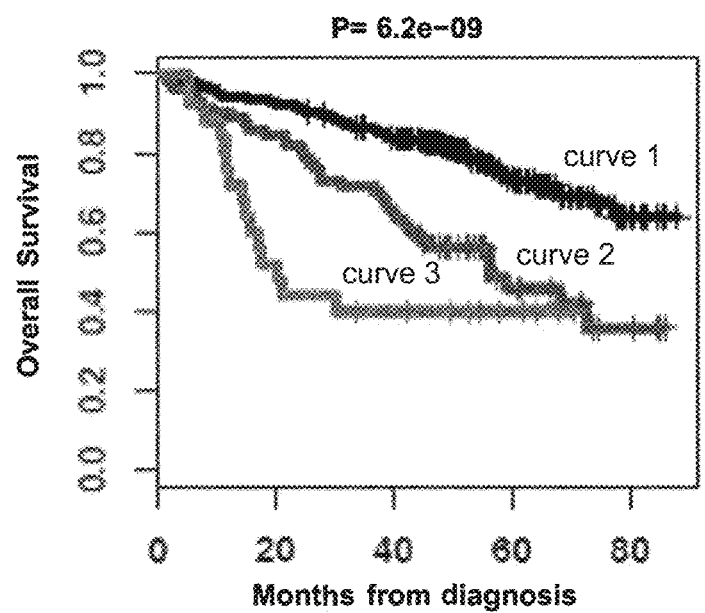
FIG. 15 is a plot illustrating the Kaplan-Meier curves of the OS of the AOX and ROS signature groups of patients of the TT2 cohort (N=345) corresponding to the scatterplot in FIG. 13. Curve 1 represents the patients with a low AOX and a low ROS risk signature, N=249 (72.2%), curve 2 represents either the patients with a high AOX and a low ROS risk signature or with a low AOX and a high ROS risk signature, N=71 (20.6%), and curve 3 represents the patients with a high AOX and a high ROS risk signature, N=25 (7.2%).

This patient's stratification reveals that patients with both high AOX and high ROS risk signatures have the most aggressive outcome (EFS and OS) as compared to the other groups. Although having low AOX risk signature, the group low AOX/high ROS signature has an adverse prognosis as compared to the patients with best outcome with low AOX/ROS risk signatures (FIG. 14 and FIG. 15).

Figure 16:
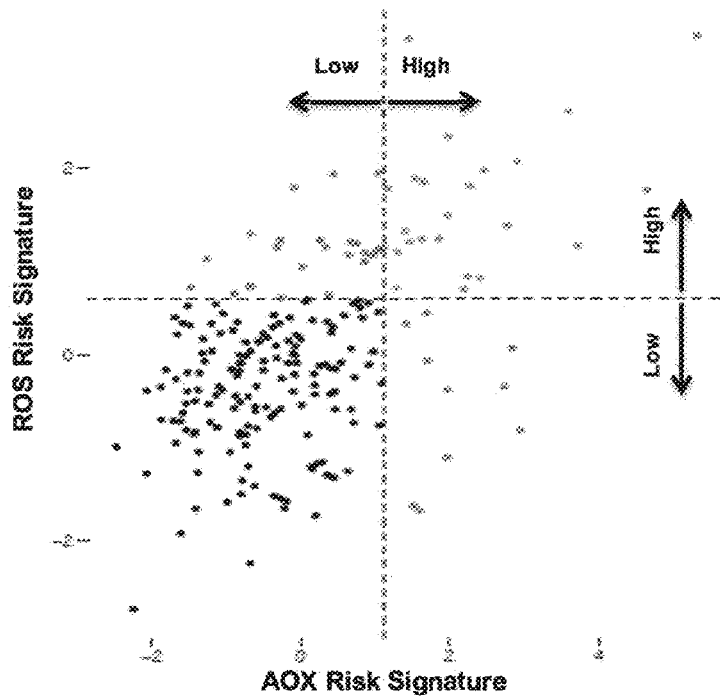
FIG. 16 is a scatter plot diagram of AOX and ROS risk signature for patients of the HM cohort (N=206).
Figure 17:
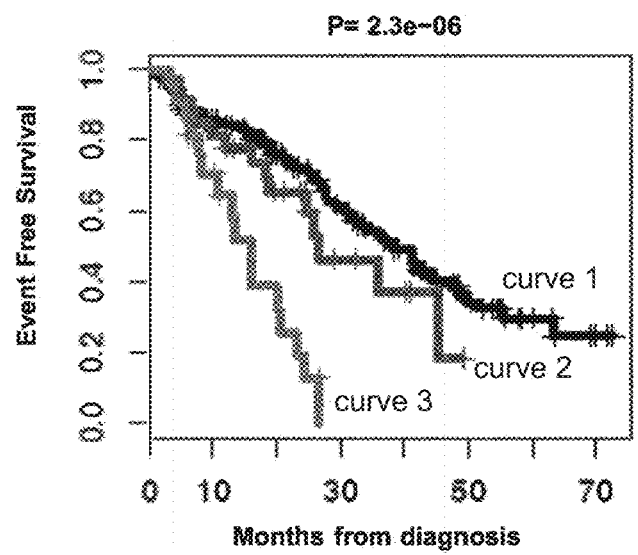
FIG. 17 is a plot illustrating the Kaplan-Meier curves of the EFS for patients of the HM cohort (N=206) corresponding to the scatterplot in FIG. 16. Curve 1 represents the patients with a low AOX and a low ROS risk signature, N=149 (72.3%), curve 2 represents either the patients with a high AOX and a low ROS risk signature or a low AOX and a high ROS risk signature, N=34 (16.5%), and curve 3 represents the patients with a high AOX and a high ROS risk signature, N=23 (11.2%).
Figure 18:
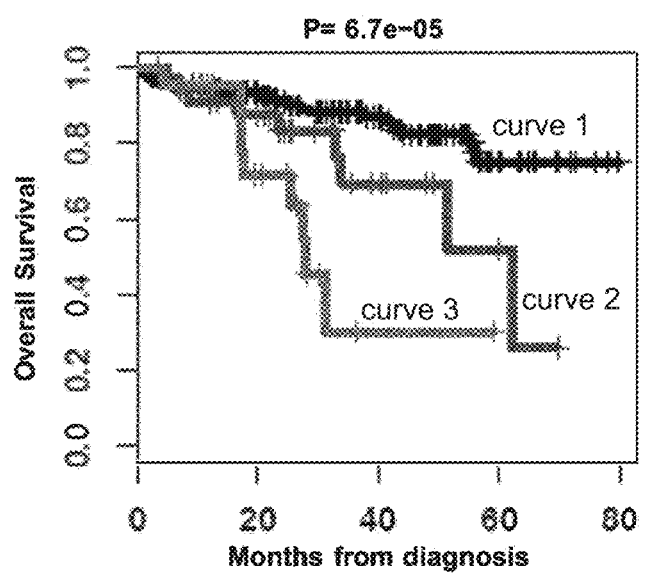
FIG. 18 is a plot illustrating the Kaplan-Meier curves of the OS for patients of the HM cohort (N=206) corresponding to the scatterplot in FIG. 16. Curve 1 represents the patients with a low AOX and a low ROS risk signature, N=149 (72.3%), curve 2 represents either the patients with a high AOX and a low ROS risk signature or a low AOX and a high ROS risk signature, N=34 (16.5%), and curve 3 represents the patients with a high AOX and a high ROS risk signature, N=23 (11.2%).

Similar finding are reported for HM cohort (FIG. 16, FIG. 17 and FIG. 18). As such, both signatures are essential to build up a molecular redox signature of the patient, which could better predict the responsiveness and treatment efficacy.

The results underscore the heterogeneity in Redox signature of MM patients from two cohorts and imply that redox status could be involved in drug resistance and could represent an interesting therapeutic target in MM.

2.3/HMCLs Redox Signature Predicts Sensitivity to MM Major Drugs

Since Melphalan and bortezomib have been previously reported to induce MMC toxicity through ROS induction, the determination of whether the AOX and ROS risk signatures could predict for the sensitivity of HMCLs to these major anti-MM drugs was investigated.

Considering the GEP of 40 HMCLs (Moreaux et al., 2011), HMCLs AOX and ROS risk signatures were determined. The 5 HMCLs with the highest (AMO1, L363, LP1, OPM2, RPMI8266) and the lowest (JJN3, XG-6, XG-19, XG-20, XG-24) AOX/ROS scores were selected to assay Melphalan and Bortezomib sensitivities (Moreaux et al., 2012 and Moreaux et al., 2013).

Figure 19:
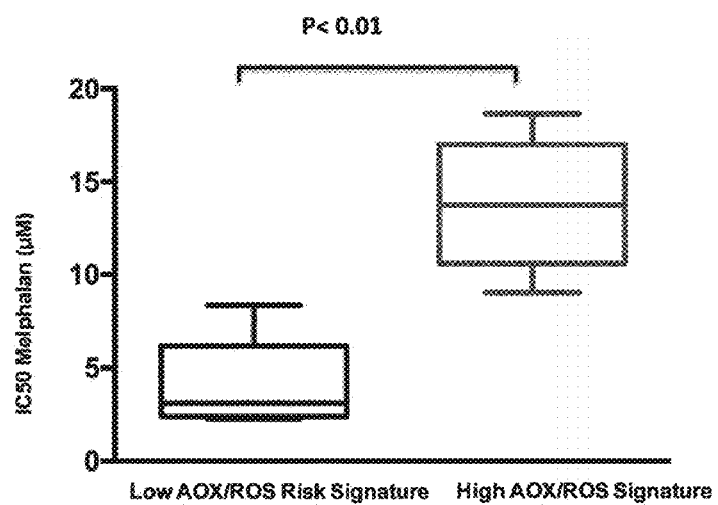
FIG. 19 is a boxplot diagram representing AOX and ROS risk signatures predicted sensitivity of human myeloma cell lines (HMCLs) to Melphalan. HMCLs with the low AOX and low ROS (low AOX/ROS) risk signature (JJN3, XG-6, XG-19, XG-20, XG-24) exhibit significantly higher Melphalan sensitivity as compared to HMCLs with high AOX and high ROS (high AOX/ROS) risk signature (AMO1, L363, LP1, OPM2, RPM18266). Ordinates represent the median of IC50 (expressed in µM) at 96h and data are mean values SD of 3 independent experiments.

HMCLs with the low AOX/ROS risk signatures exhibited a significant 4-fold higher Melphalan sensitivity (p<0.003, Median IC50=3.11 µM, range, 2.25-8.34 µM) as compared to HMCLs with high AOX/ROS risk signatures (p<0.01, Median IC50=13.74 µM, range: 9.02-18.65 µM) (FIG. 19).

Figure 20:
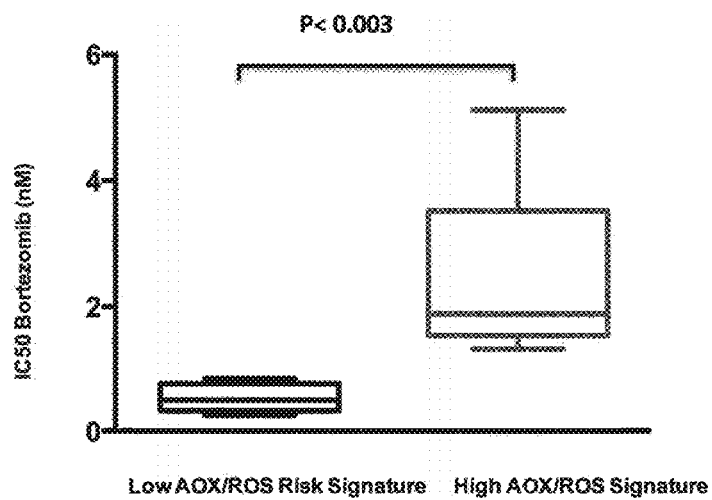
FIG. 20 is a boxplot diagram representing AOX and ROS risk signatures predicted sensitivity of HMCLs to Bortezomib. HMCLs with the low AOX and low ROS (low AOX/ROS) risk signature (JJN3, XG-6, XG-19, XG-20, XG-24) exhibit significantly higher Bortezomib (B) sensitivity as compared to HMCLs with high AOX and high ROS (high AOX/ROS) risk signature (AMO1, L363, LP1, OPM2, RPM18266). Ordinates represent the median of IC50 (expressed in nM) at 96h and data are mean values SD of 3 independent experiments.

Similar findings are reported for Bortezomib where low AOX/ROS risk signatures HMCLs exhibited a significant 3.5-fold higher sensitivity (p<0.003, Median IC50=0.51 nM, Range: 0.27-0.85 nM) than HMCLs with low AOX/ROS risk signatures (Median IC50=1.87 nM, range: 1.31-5.11 nM) (FIG. 20).

Figure 21:
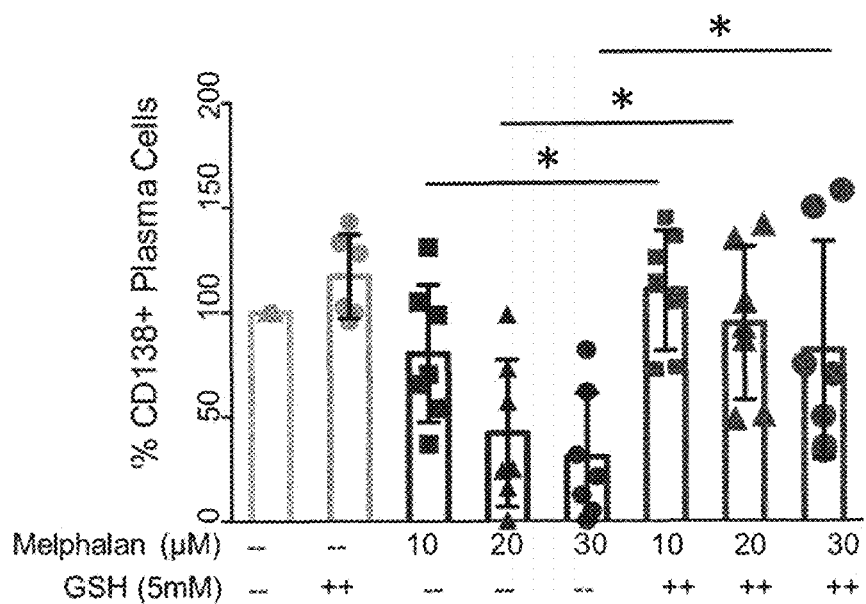
FIG. 21 is plot diagram illustrating antioxidants protection of CD138$^+$ cells from patients after treatment with Melphalan. GSH protects CD138$^+$ cells from Melphalan-induced toxicity. Cells from bone marrow samples from 10 patients were treated without (--) or with 10, 20 and 30 µM of Melphalan, in the presence (++) or the absence (--) of 5 mM glutathione (GSH). After 5 days the percentage and absolute number of CD138$^+$ cells was assessed by flow cytometry using an anti-CD138 APC antibody. * indicates a significant difference using a Student test for pairs (P≤0.05).
Figure 22:
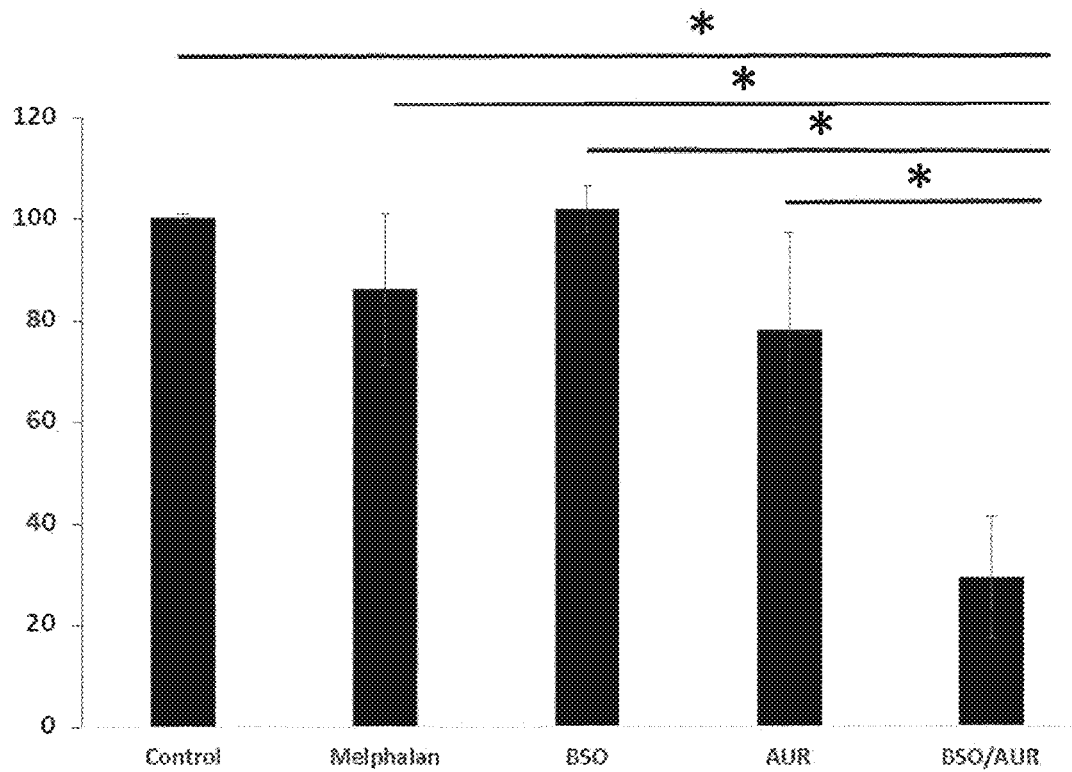
FIG. 22 is a plot diagram illustrating the synergistic effect to eradicate myeloma cells by targeting Gluthathione-Thioredoxin system. Cells from bone marrow samples from 3 patients were treated with 10 µM Melphalan, 250 nM Auranofin (AUR), 250 µM BSO or a combination of 250 nM Auranofin and 250 µM BSO (BSO/AUR). After 5 days the percentage and absolute number of CD138+ cells were assessed by flow cytometry using an anti-CD138 APC antibody. * indicates a significant difference using a Student test for pairs (P≤0.05).
Figure 23:
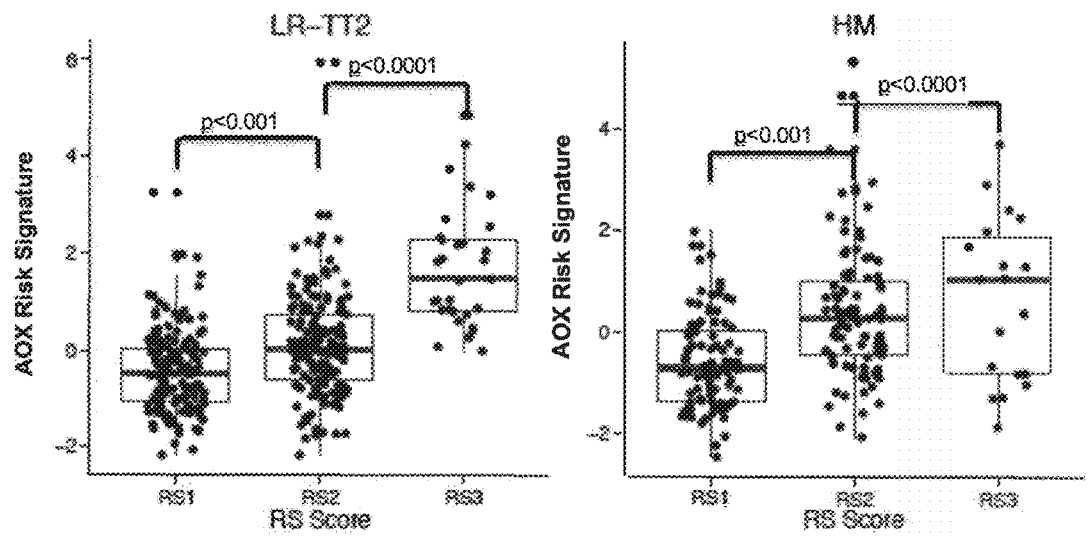
FIG. 23 is box plot diagram illustrating the comparison between the AOX risk signature and the previously established Risk Score (RS Score). The left panel represents the LR-TT2 cohort and the right panel represents the HM cohort.
Figure 24:
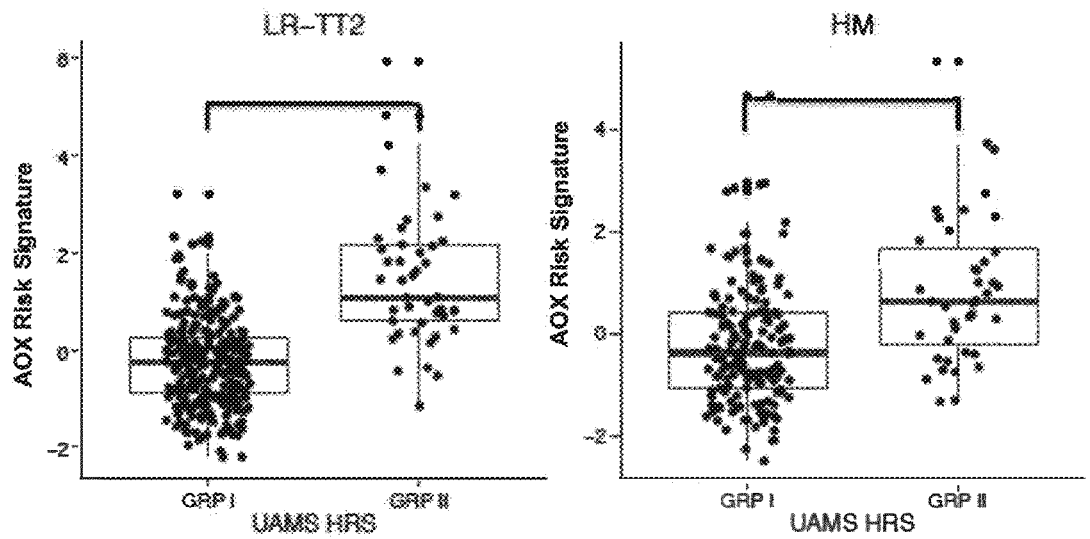
FIG. 24 is box plot diagram illustrating the comparison between the AOX risk signature and the previously established UAMS-HRS (UAMS-HRS, high-risk score from UAMS). The left panel represents the LR-TT2 cohort and the right panel represents the HM cohort.
Figure 25:
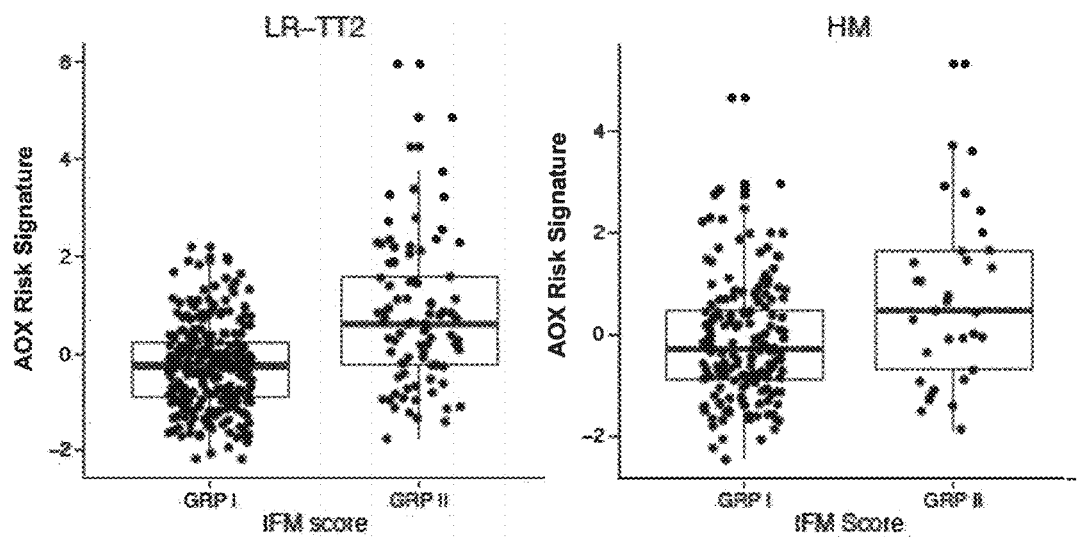
FIG. 25 is a box plot diagram illustrating the comparison between the AOX risk signature and the previously established IFM Score (IFM, Intergroupe Francophone du Myelome). The left panel represents the LR-TT2 cohort and the right panel represents the HM cohort.
Figure 26:
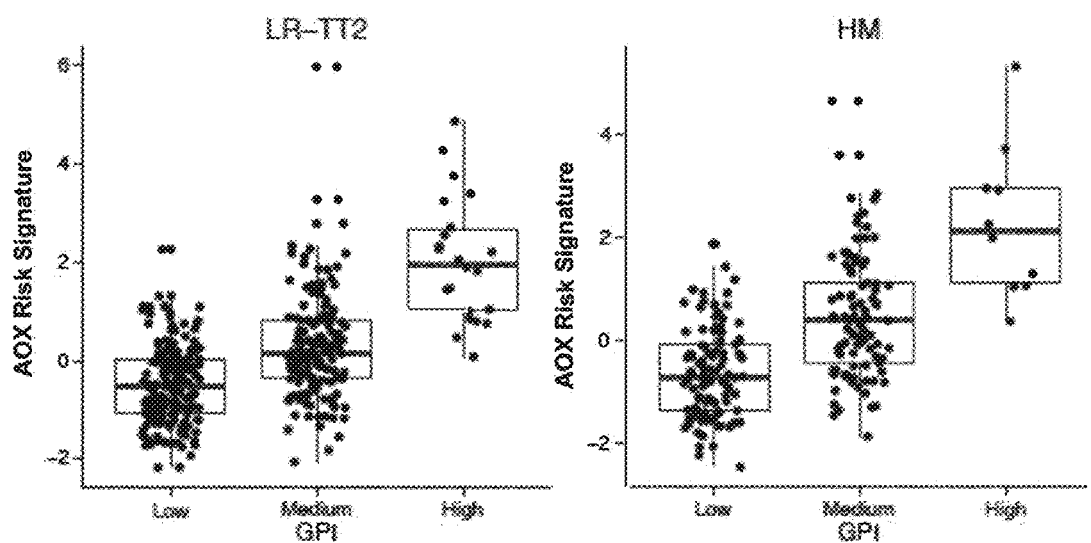
FIG. 26 is a box plot diagram illustrating the comparison between the AOX risk signature and the previously established GPI Score (GPI, gene expression based proliferation index). The left panel represents the LR-TT2 cohort and the right panel represents the HM cohort.
Figure 27:
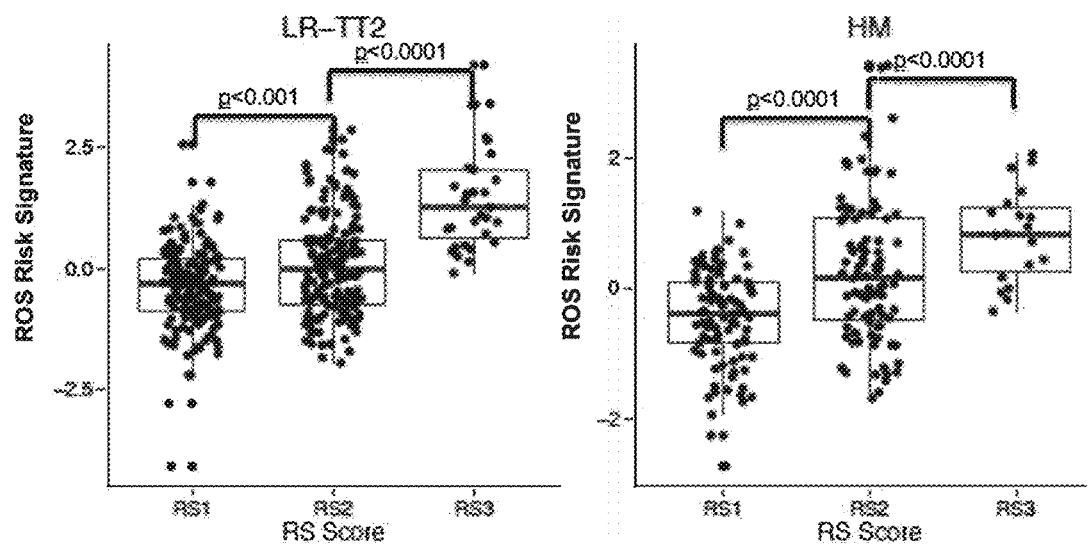
FIG. 27 is a box plot diagram illustrating the comparison between the ROS risk signature and the previously established Risk Score. The left panel represents the LR-TT2 cohort and the right panel represents the HM cohort.
Figure 28:
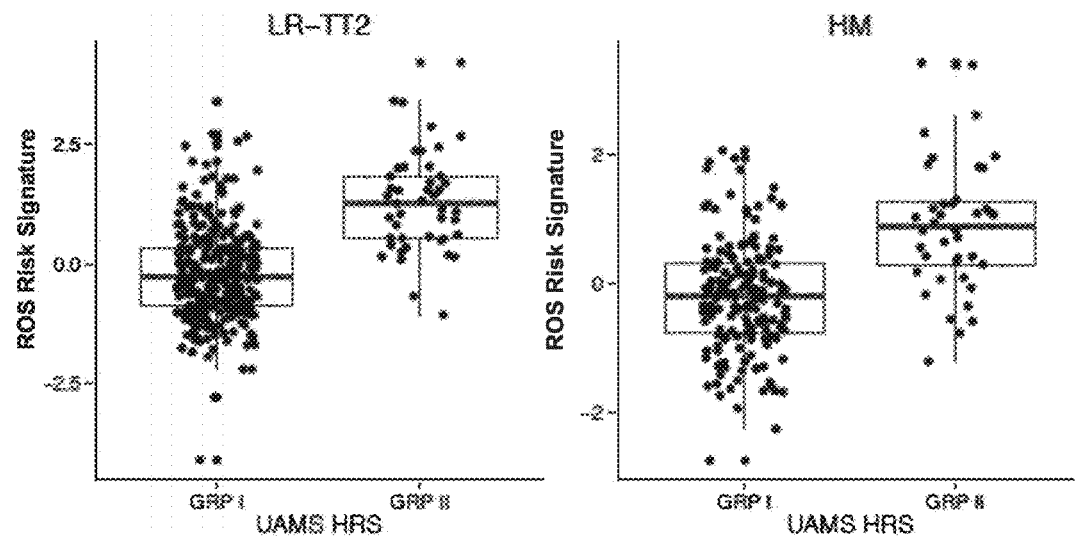
FIG. 28 is a box plot diagram illustrating the comparison between the ROS risk signature and the previously established UAMS-HRS (UAMS-HRS, high-risk score from UAMS). The left panel represents the LR-TT2 cohort and the right panel represents the HM cohort.
Figure 29:
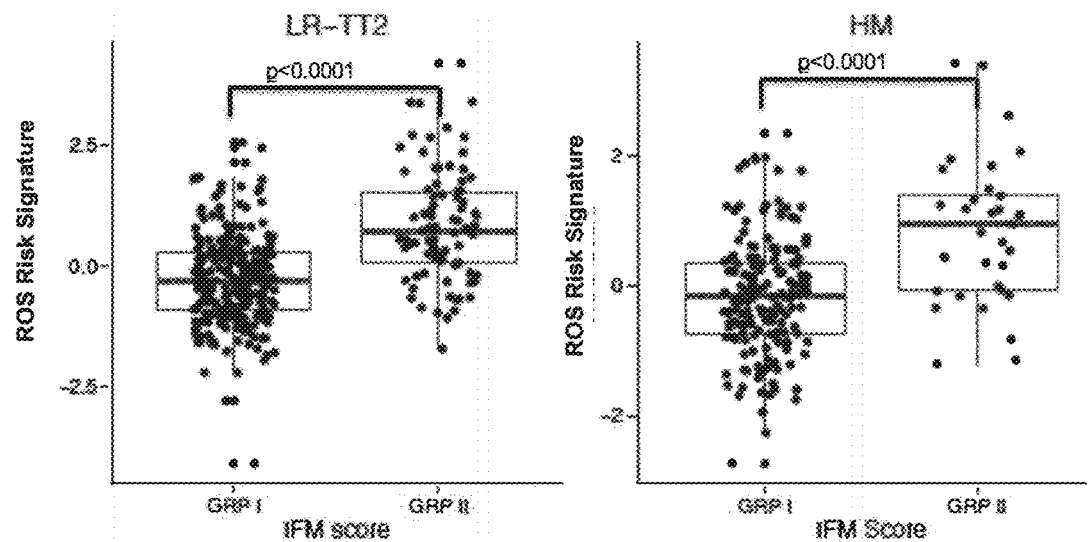
FIG. 29 is a box plot diagram illustrating the comparison between the ROS risk signature and the previously established IFM Score (IFM, Intergroupe Francophone du Myelome). The left panel represents the LR-TT2 cohort and the right panel represents the HM cohort.
Figure 30:
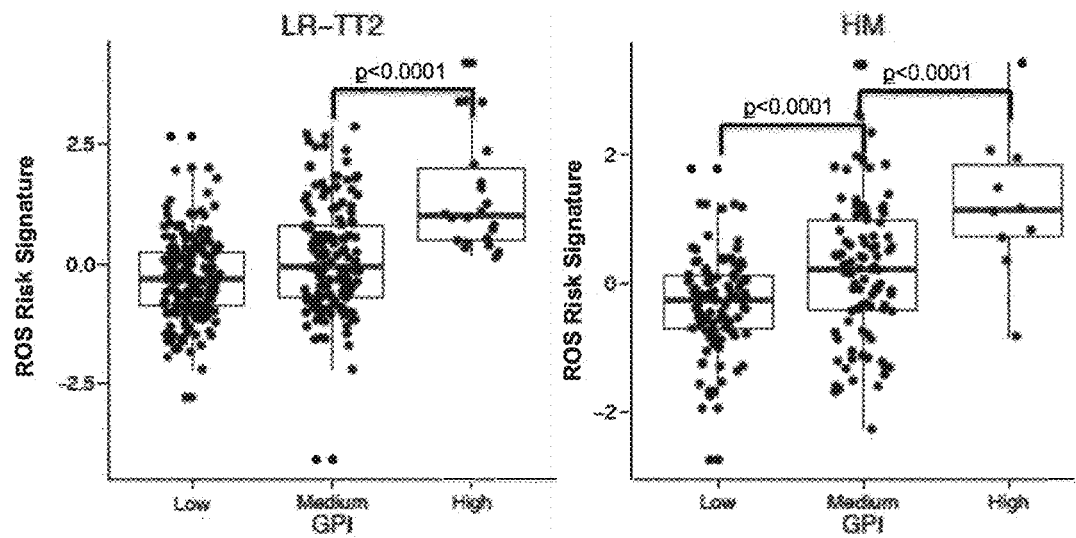
FIG. 30 is a plot diagram illustrating the comparison between the ROS risk signature and the previously established GPI Score (GPI, gene expression based proliferation index). The left panel represents the LR-TT2 cohort and the right panel represents the HM cohort.

According to these observations, treatment of MM cell lines with physiological concentrations of gluthatione (GSH) antioxidant significantly protect primary myeloma cells from patients (n=10) from melphalan induced apoptosis. (p<0.05) (FIG. 21). Furthermore, targeting the Gluthatione-Thioredoxin system with Thioredoxin system inhibitor (Auranofin) and Glutathione system inhibitor (BSO) has a synergistic toxicity on primary MM cells from patients (n=3; p<0.05) (FIG. 22).

2.4/Validation of the AOX and ROS Risk Signatures Over the Previously Reported Signatures Furthermore, using multivariate Cox multivariate analysis, prognostic value for EFS of AOX and ROS risk signatures were compared with usual prognostic factors—ISS, t(4;14), del17p, GEP-based risk scores, UAMS-HRS (Shaughnessy et al., 2007), IFM score (Decaux et al., 2008), GPI (Hose et al., 2010) and RS score (Reme et al., 2013). Results showed that AOX and ROS risk signatures are independent of previously established prognostic scores (p<0.005) but yet they are significantly correlated (AOX: FIG. 23 to FIG. 26; ROS: FIG. 27 to FIG. 30).

CITATION LIST

Barlogie B. Total therapy 2 without thalidomide in comparison with total therapy 1: role of intensified induction and posttransplantation consolidation therapies. Blood 2006; 107:2633-8.

Decaux O, Lode L, Magrangeas F, Charbonnel C, Gouraud W, Jezequel P, Attal M, Harousseau J L, Moreau P, Bataille R, et al. Prediction of Survival in Multiple Myeloma Based on Gene Expression Profiles Reveals Cell Cycle and Chromosomal Instability Signatures in High-Risk Patients and Hyperdiploid Signatures in Low-Risk Patients: A Study of the Intergroupe Francophone du Myelome. J Clin Oncol 2008; 26:4798-805.

DeNicola G M, Karreth F A, Humpton T J, Gopinathan A, Wei C, Frese K, Mangal D, Yu K H, Yeo C J, Calhoun E S, et al. Oncogene-induced Nrf2 transcription promotes ROS detoxification and tumorigenesis. Nature 2012; 475: 106-9.

Diehn M, Cho R W, Lobo N A, Kalisky T, Dorie M J, Kulp A N, Qian D, Lam J S, Ailles L E, Wong M, et al. Association of reactive oxygen species levels and radioresistance in cancer stem cells. Nature 2009; 458:780-3.

Goldschmidt H, Sonneveld P, Cremer F W, van der Holt B, Westveer P, Breitkreutz I, Benner A, Glasmacher A, Schmidt-Wolf I G D, Martin H, et al. Joint HOVON-50/ GMMG-HD3 randomized trial on the effect of thalidomide as part of a high-dose therapy regimen and as maintenance treatment for newly diagnosed myeloma patients. Ann Hematol 2003; 82:654-9.

Hose D, Reme T, Hielscher T, Moreaux J, Messner T, Seckinger A, Benner A, Shaughnessy J D, Barlogie B, Zhou Y, et al. Proliferation is a central independent prognostic factor and target for personalized and risk-adapted treatment in multiple myeloma. Haematologica 2010; 96:87-95.

Irwin M E, Rivera-Del Valle N, Chandra J. Redox Control of Leukemia: From Molecular Mechanisms to Therapeutic Opportunities. Antioxidants & Redox Signaling 2013; 18:1349-83.

Kassambara A, Rème T, Jourdan M, Fest T, Hose D, Tarte K, Klein B. GenomicScape: An Easy-to-Use Web Tool for Gene Expression Data Analysis. Application to Investigate the Molecular Events in the Differentiation of B Cells into Plasma Cells. PLOS Comput Biol 2015; 11:e1004077.

Kobayashi C I, Suda T. Regulation of reactive oxygen species in stem cells and cancer stem cells. J Cell Physiol 2011; 227:421-30.

Moreaux J, Reme T, Leonard W, Veyrune J L, Requirand G, Goldschmidt H, Hose D, Klein B. Gene expression-based prediction of myeloma cell sensitivity to histone deacetylase inhibitors. Br J Cancer. 2013 Aug. 6; 109(3):676-85

Moreaux J, Rème T, Leonard W, Veyrune J L, Requirand G, Goldschmidt H, Hose D, Klein B. Development of gene expression-based score to predict sensitivity of multiple myeloma cells to DNA methylation inhibitors. Mol Cancer Ther. 2012 December; 11(12):2685-92.

Moreaux J, Klein B, Bataille R, Descamps G, Maiga S, Hose D, Goldschmidt H, Jauch A, Reme T, Jourdan M, et al. A high-risk signature for patients with multiple myeloma established from the molecular classification of human myeloma cell lines. Haematologica 2011; 96:574-82.

Mulligan G, Mitsiades C, Bryant B, Zhan F, Chng W J, Roels S, Koenig E, Fergus A, Huang Y, Richardson P, Trepicchio W L, Broyl A, Sonneveld P, Shaughnessy J D Jr, Bergsagel P L, Schenkein D, Esseltine D L, Boral A, Anderson K C. Gene expression profiling and correlation with outcome in clinical trials of the proteasome inhibitor bortezomib. Blood. 2007 Apr. 15; 109(8):3177-88.

Reme T, Hose D, Theillet C, Klein B. Modeling risk stratification in human cancer. Bioinformatics 2013; 29:1149-57.

Ren F, Wang K, Zhang T, Jiang J, Nice E C, Huang C. Biochimica et Biophysica Acta. BBA—General Subjects 2015; 1850:1518-26.

Sharma A, Tripathi M, Satyam A, Kumar L. Study of antioxidant levels in patients with multiple myeloma. Leuk Lymphoma 2009; 50:809-15.

Shaughnessy J D Jr, Zhan F, Burington B E, Huang Y, Colla S, Hanamura I, Stewart J P, Kordsmeier B, Randolph C, Williams D R, Xiao Y, Xu H, Epstein J, Anaissie E, Krishna S G, Cottler-Fox M, Hollmig K, Mohiuddin A, Pineda-Roman M, Tricot G, van Rhee F, Sawyer J, Alsayed Y, Walker R, Zangari M, Crowley J, Barlogie B. A validated gene expression model of high-risk multiple myeloma is defined by deregulated expression of genes mapping to chromosome 1. Blood. 2007 Mar. 15; 109(6): 2276-84.

Sporn M B, Liby K T. NRF2 and cancer: the good, the bad and the importance of context. Nat Rev Cancer 2012; 12:564-71.

Tarte K, Zhang X G, Legouffe E, Hertog C, Mehtali M, Rossi J F, Klein B. Induced expression of B7-1 on myeloma cells following retroviral gene transfer results in tumor-specific recognition by cytotoxic T cells. J Immunol. 1999 Jul. 1; 163(1):514-24.

Urao N, Ushio-Fukai M. Free Radical Biology and Medicine. Free Radical Biology and Medicine 2013; 54:26-39.

Wang K, Zhang T, Dong Q, Nice E C, Huang C, Wei Y. Redox homeostasis: the linchpin in stem cell self-renewal and differentiation. Cell Death and Disease 2013; 4:e537-10.

Ye Z-W, Zhang J, Townsend D M, Tew K D. Biochimica et Biophysica Acta. BBA—General Subjects 2015; 1850: 1607-21.

The invention claimed is:

1. A method for treating an individual having a multiple myeloma and who is able to respond to a therapeutic anti-multiple myeloma (anti-MM) treatment, comprising the steps of:
   a) identifying the individual able to respond to the therapeutic anti-MM treatment by performing the following steps:
   i) measuring the expression level of at least 2 genes encoding a reactive oxygen species, or ROS, detoxifying (AOX) protein selected in a group consisting of AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN and the expression level of at least 2 genes encoding a ROS producing (ROS) protein selected in a group consisting of CYBA, CYB5A, CYC1, NCF1B, NCF1C, NCF4, NDUFA12, NDUFS2, NDUFS8, SHC1 and UQCR10, in a blood or plasma sample obtained from said individual;
   ii) calculating an AOX score value and a ROS score value from the said respective expression levels obtained at step i);
   iii) comparing said AOX score value and/or said ROS score value to a respective predetermined reference value; and
   iv) confirming that said AOX score value and/or said ROS score value is lower than the respective predetermined reference value and concluding that said individual is able to respond to said therapeutic anti-MM treatment, and
   b) administering to said individual an effective amount of said therapeutic anti-MM treatment, wherein said therapeutic anti-MM treatment comprises at least one anticancer compound selected from the group consisting of bortezomib, melphalan, a proteosome inhibitor, a cytostatic alkylating agent, and combinations thereof.

2. The method according to claim 1, wherein the expression level of 16 genes encoding a ROS detoxifying (AOX) protein consisting of AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and/or the expression level of 11 genes encoding ROS producing (ROS) protein consisting of CYBA, CYB5A, CYC1, NCF4, NCF1B, NCF1C, NDUFA12, NDUFS2, NDUFS8, SHC1 and UQCR10, is measured at step i).

3. The method according to claim 1, wherein the expression level of 16 genes encoding a ROS detoxifying (AOX) protein consisting of AKR1B1, ARNT, CAT, CBR1, DHCR24, EGLN1, GLRX2, HIF1A, MGST1, MSRB1, PRDX6, SLC7A11, SOD1, SRXN1, TALDO1 and TXN, and the expression level of 11 genes encoding ROS producing (ROS) protein consisting of CYBA, CYB5A, CYC1, NCF4, NCF1B, NCF1C, NDUFA12, NDUFS2, NDUFS8, SHC1 and UQCR10, is measured at step i).

4. The method according to claim 1, wherein the at least one anticancer compound is selected from the group consisting of melphalan, and combinations thereof.

5. The method according to claim 4, wherein the at least one anticancer compound is bortezomib.

6. The method according to claim 5, wherein the at least one anticancer compound is melphalan.

7. The method according to claim 1, wherein the at least one anticancer compound is a proteosome inhibitor.

8. The method according to claim 1, wherein the at least one anticancer compound is a cytostatic alkylating agent.

\* \* \* \* \*